US010029102B2

(12) United States Patent
Doan et al.

(10) Patent No.: US 10,029,102 B2
(45) Date of Patent: Jul. 24, 2018

(54) SYSTEM AND METHOD FOR DELIVERING MODULATED SUB-THRESHOLD THERAPY TO A PATIENT

(71) Applicant: Boston Scientific Neuromodulation Corporation, Valencia, CA (US)

(72) Inventors: Que T. Doan, West Hills, CA (US); Jordi Parramon, Valencia, CA (US); Sridhar Kothandaraman, Valencia, CA (US); Christopher Ewan Gillespie, Stevenson Ranch, CA (US); Sarvani Grandhe, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 836 days.

(21) Appl. No.: 14/296,056

(22) Filed: Jun. 4, 2014

(65) Prior Publication Data
US 2014/0364920 A1 Dec. 11, 2014

Related U.S. Application Data

(60) Provisional application No. 61/909,915, filed on Nov. 27, 2013, provisional application No. 61/832,088, filed on Jun. 6, 2013.

(51) Int. Cl.
A61N 1/36 (2006.01)
A61N 1/372 (2006.01)
A61N 1/32 (2006.01)

(52) U.S. Cl.
CPC ..... A61N 1/36164 (2013.01); A61N 1/36071 (2013.01); A61N 1/36139 (2013.01);
(Continued)

(58) Field of Classification Search
CPC ............ A61N 1/36071; A61N 1/36185; A61N 1/37247; A61N 1/36139; A61N 1/36164;
(Continued)

(56) References Cited

U.S. PATENT DOCUMENTS 6,516,227 B1 2/2003 Meadows et al.
6,675,046 B2 1/2004 Holsheimer
(Continued)

FOREIGN PATENT DOCUMENTS

WO WO-2006029257 A2 3/2006
WO WO-2006092061 A1 9/2006
(Continued)

OTHER PUBLICATIONS

Rao, Prakash, et al., "Technique for Linking Electrodes Together During Programming of Neurostimulation System", U.S. Appl. No. 61/561,760, filed Nov. 18, 2011.
(Continued)

Primary Examiner — Christopher D Koharski
Assistant Examiner — Pamela M Bays
(74) Attorney, Agent, or Firm — Schwegman Lundberg & Woessner, P.A.

(57) ABSTRACT

A neuromodulation system and method of providing therapy to a patient. Electrical energy is delivered to the patient in accordance with a modulation parameter, thereby providing therapy to the patient, and the modulation parameter of the delivered electrical energy is varied over a period of time, such that the delivered electrical energy is continually maintained at a sub-threshold level throughout the period of time. The sub-threshold level may be referred to as a patient-perception threshold, which may be referred to as a boundary below which a patient does not sense delivery of the electrical energy. For example, in a spinal cord modulation system, the patient-perception threshold may be a boundary below which a patient does not experience paresthesia.

24 Claims, 10 Drawing Sheets

(52) U.S. Cl.
CPC ..... *A61N 1/36178* (2013.01); *A61N 1/36185* (2013.01); *A61N 1/36189* (2013.01); *A61N 1/37241* (2013.01); *A61N 1/37247* (2013.01)

(58) Field of Classification Search
CPC ............ A61N 1/36187; A61N 1/36132; A61N 1/36189; A61N 1/37241; A61N 1/0551; A61N 1/36178
USPC .......................................................... 607/46
See application file for complete search history.

(56) References Cited

U.S. PATENT DOCUMENTS

| | | | |
|---|---|---|---|
| 6,895,280 | B2 | 5/2005 | Meadows et al. |
| 6,993,384 | B2 | 1/2006 | Bradley et al. |
| 7,317,948 | B1 | 1/2008 | King et al. |
| 7,333,857 | B2 | 2/2008 | Campbell |
| 7,539,538 | B2 | 5/2009 | Parramon et al. |
| 7,650,184 | B2 | 1/2010 | Walter |
| 7,979,133 | B2 | 7/2011 | Feler et al. |
| 8,019,439 | B2 | 9/2011 | Kuzma et al. |
| 8,224,453 | B2 | 7/2012 | De Ridder |
| 8,255,057 | B2 | 8/2012 | Fang et al. |
| 8,355,797 | B2 | 1/2013 | Caparso et al. |
| 8,380,318 | B2 | 2/2013 | Kishawi et al. |
| 8,455,716 | B2 | 6/2013 | Huang et al. |
| 8,504,147 | B2 | 8/2013 | Deem et al. |
| 8,615,300 | B2 | 12/2013 | Feler et al. |
| 8,649,874 | B2 | 2/2014 | Alataris et al. |
| 8,670,831 | B2 | 3/2014 | Wacnik et al. |
| 8,676,329 | B2 | 3/2014 | Wacnik et al. |
| 8,676,331 | B2 | 3/2014 | Parker |
| 8,731,675 | B2 | 5/2014 | Ranu et al. |
| 8,751,009 | B2 | 6/2014 | Wacnik |
| 2003/0139781 | A1 | 7/2003 | Bradley et al. |
| 2004/0034394 | A1 | 2/2004 | Woods et al. |
| 2007/0150036 | A1 | 6/2007 | Anderson |
| 2008/0188909 | A1 | 8/2008 | Bradley |
| 2009/0204173 | A1 | 8/2009 | Fang et al. |
| 2010/0010566 | A1 | 1/2010 | Thacker et al. |
| 2010/0023069 | A1* | 1/2010 | Moffitt ............... A61N 1/36071 607/2 |
| 2010/0023090 | A1* | 1/2010 | Jaax ................... A61N 1/37264 607/59 |
| 2010/0121409 | A1 | 5/2010 | Kothandaraman et al. |
| 2010/0249875 | A1 | 9/2010 | Kishawi et al. |
| 2010/0274312 | A1* | 10/2010 | Alataris ............. A61N 1/36071 607/46 |
| 2010/0274314 | A1 | 10/2010 | Alataris et al. |
| 2010/0274315 | A1 | 10/2010 | Alataris et al. |
| 2010/0274317 | A1* | 10/2010 | Parker ................ A61N 1/36071 607/46 |
| 2010/0274318 | A1 | 10/2010 | Walker et al. |
| 2010/0274326 | A1 | 10/2010 | Chitre et al. |
| 2012/0059446 | A1 | 3/2012 | Wallace et al. |
| 2012/0083709 | A1 | 4/2012 | Parker et al. |
| 2012/0253422 | A1 | 10/2012 | Thacker et al. |
| 2012/0265279 | A1 | 10/2012 | Zhu |
| 2012/0283797 | A1 | 11/2012 | De Ridder |
| 2012/0290041 | A1 | 11/2012 | Kim et al. |
| 2013/0066411 | A1 | 3/2013 | Thacker et al. |
| 2013/0116752 | A1 | 5/2013 | Parker et al. |
| 2013/0131760 | A1 | 5/2013 | Rao et al. |
| 2013/0268021 | A1 | 10/2013 | Moffitt |
| 2013/0296975 | A1 | 11/2013 | Lee et al. |
| 2014/0081349 | A1 | 3/2014 | Lee et al. |
| 2014/0277267 | A1 | 9/2014 | Vansickle et al. |

FOREIGN PATENT DOCUMENTS

| | | |
|---|---|---|
| WO | WO-2006135791 A2 | 12/2006 |
| WO | WO-2008095185 A1 | 8/2008 |
| WO | WO-2014197596 A1 | 12/2014 |

OTHER PUBLICATIONS

Vansickle, Dennis Allen, et al., "Neuromodulation System and Method for Transitioning Between Programming Modes", U.S. Appl. No. 14/214,752, filed Mar. 15, 2014.
Vansickle, Dennis Allen, "Systems and Methods for Delivering Sub-Threshold Therapy to a Patient", U.S. Appl. No. 61/801,917, filed Mar. 15, 2013.
"Australian Application Serial No. 2014274966, First Examiner Report dated Nov. 11, 2017", 3 pgs.
"International Application Serial No. PCT/US2014/40910, International Preliminary Report on Patentability dated Dec. 17, 2015", 8 pgs.
"International Application Serial No. PCT/US2014/40910, International Search Report dated Sep. 19, 2014", 4 pgs.
"International Application Serial No. PCT/US2014/40910, Written Opinion dated Sep. 19, 2014", 6 pgs.
"Australian Application Serial No. 2014274966, Response filed Dec. 1, 2017 to Subsequent Examiners Report dated Nov. 21, 2017", 15 pgs.
"Australian Application Serial No. 2014274966, Response filed Dec. 14, 2017 to Subsequent Examiners Report dated Dec. 7, 2017", 17 pgs.
"Australian Application Serial No. 2014274966, Subsequent Examiners Report dated Nov. 21, 2017", 4 pgs.
"Australian Application Serial No. 2014274966, Subsequent Examiners Report dated Dec. 7, 2017", 4 pgs.

\* cited by examiner

SYSTEM AND METHOD FOR DELIVERING MODULATED SUB-THRESHOLD THERAPY TO A PATIENT

CLAIM OF PRIORITY

This application claims the benefit of priority under 35. U.S.C. § 119(e) of U.S. Provisional Patent Application Ser. No. 61/909,915, filed on Nov. 27, 2013, which claims the benefit of priority under 35. U.S.C. § 119(e) of U.S. Provisional Patent Application Ser. No. 61/832,088, filed on Jun. 6, 2013, each of which is herein incorporated by reference in its entirety.

FIELD OF THE INVENTION

The present inventions relate to tissue modulation systems, and more particularly, to programmable neuromodulation systems.

BACKGROUND OF THE INVENTION

Implantable neuromodulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems, such as the Freehand system by NeuroControl (Cleveland, Ohio), have been applied to restore some functionality to paralyzed extremities in spinal cord injury patients.

These implantable neuromodulation systems typically include one or more electrode carrying stimulation leads, which are implanted at the desired stimulation site, and an implantable neuromodulation device (e.g., an implantable pulse generator (IPG)) implanted remotely from the stimulation site, but coupled either directly to the neuromodulation lead(s) or indirectly to the neuromodulation lead(s) via a lead extension. The neuromodulation system may further comprise a handheld external control device (e.g., a remote control (RC)) to remotely instruct the neuromodulator to generate electrical stimulation pulses in accordance with selected stimulation parameters.

Electrical modulation energy may be delivered from the neuromodulation device to the electrodes in the form of an electrical pulsed waveform. Thus, electrical energy may be controllably delivered to the electrodes to therapeutically modulate neural tissue. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. Other parameters that may be controlled or varied include the amplitude, width, and rate of the electrical pulses (which may be considered electrical pulse parameters) provided through the electrode array. Each electrode configuration, along with the electrical pulse parameters, can be referred to as a "modulation parameter set."

With some neuromodulation systems, and in particular, those with independently controlled current or voltage sources, the distribution of the current to the electrodes (including the case of the neuromodulation device, which may act as an electrode) may be varied such that the current is supplied via numerous different electrode configurations. In different configurations, the electrodes may provide current or voltage in different relative percentages of positive and negative current or voltage to create different electrical current distributions (i.e., fractionalized electrode configurations).

As briefly discussed above, an external control device can be used to instruct the neuromodulation device to generate electrical pulses in accordance with the selected modulation parameters. Typically, the modulation parameters programmed into the neuromodulation device can be adjusted by manipulating controls on the handheld external control device to modify the electrical modulation energy provided by the neuromodulation device system to the patient. Thus, in accordance with the modulation parameters programmed by the external control device, electrical pulses can be delivered from the neuromodulation device to the electrode(s) to modulate a volume of tissue in accordance with a set of modulation parameters and provide the desired efficacious therapy to the patient. The best modulation set will typically be one that delivers modulation energy to the volume of tissue that must be modulated in order to provide the therapeutic benefit (e.g., treatment of pain), while minimizing the volume of non-target tissue that is modulated.

However, the number of electrodes available combined with the ability to generate a variety of complex electrical pulses, presents a huge selection of modulation parameter sets to the clinician or patient. For example, if the neuromodulation system to be programmed has an array of sixteen electrodes, millions of modulation parameter sets may be available for programming into the neuromodulation system. Today, neuromodulation systems may have up to thirty-two electrodes, thereby exponentially increasing the number of modulation parameters sets available for programming.

To facilitate such selection, the clinician generally programs the neuromodulation device through a computerized programming system. This programming system can be a self-contained hardware/software system, or can be defined predominantly by software running on a standard personal computer (PC). The PC or custom hardware may actively control the characteristics of the electrical stimulation generated by the neuromodulation device to allow the optimum stimulation parameters to be determined based on patient feedback or other means and to subsequently program the neuromodulation device with the optimum modulation parameter sets.

For example, in order to achieve an effective result from conventional SCS, the lead or leads must be placed in a location, such that the electrical modulation energy (in this case, electrical stimulation energy) creates a sensation known as paresthesia, which can be characterized as an alternative sensation that replaces the pain signals sensed by the patient. The paresthesia induced by the stimulation and perceived by the patient should be located in approximately the same place in the patient's body as the pain that is the target of treatment. If a lead is not correctly positioned, it is possible that the patient will receive little or no benefit from an implanted SCS system. Thus, correct lead placement can mean the difference between effective and ineffective pain therapy. When electrical leads are implanted within the patient, the computerized programming system, in the context of an operating room (OR) mapping procedure, may be used to instruct the neuromodulation device to apply electrical stimulation to test placement of the leads and/or electrodes, thereby assuring that the leads and/or electrodes are implanted in effective locations within the patient.

Once the leads are correctly positioned, a fitting procedure, which may be referred to as a navigation session, may be performed using the computerized programming system to program the external control device, and if applicable the neuromodulation device, with a set of modulation parameters that best addresses the painful site. Thus, the navigation session may be used to pinpoint volume of activation (VOA) or areas correlating to the pain. Such programming ability is particularly advantageous for targeting the tissue during implantation, or after implantation should the leads gradually or unexpectedly move that would otherwise relocate the stimulation energy away from the target site. By reprogramming the neuromodulation device (typically by independently varying the stimulation energy on the electrodes), the volume of activation (VOA) can often be moved back to the effective pain site without having to re-operate on the patient in order to reposition the lead and its electrode array. When adjusting the volume of activation (VOA) relative to the tissue, it is desirable to make small changes in the proportions of current, so that changes in the spatial recruitment of nerve fibers will be perceived by the patient as being smooth and continuous and to have incremental targeting capability.

Although alternative or artifactual sensations are usually tolerated relative to the sensation of pain, patients sometimes report these sensations to be uncomfortable, and therefore, they can be considered an adverse side-effect to neuromodulation therapy in some cases. Because the perception of paresthesia has been used as an indicator that the applied electrical energy is, in fact, alleviating the pain experienced by the patient, the amplitude of the applied electrical energy is generally adjusted to a level that causes the perception of paresthesia. It has been shown, however, that the delivery of sub-threshold electrical energy (e.g., high frequency pulsed electrical energy and/or low pulse width electrical energy) can be effective in providing neuromodulation therapy for chronic pain without causing paresthesia.

Although sub-threshold modulation therapies have shown good efficacy in early studies, because there is a lack of paresthesia that may otherwise indicate that the delivered sub-threshold electrical energy is optimized, or at least efficacious, it is difficult to immediately determine if the delivered sub-threshold therapy is optimized in terms of providing efficacious therapy. Thus, identifying an efficacious modulation parameter set for sub-threshold therapy may take several days, if not weeks, requiring several reprogramming sessions with the clinician.

There, thus, remains a need to provide a means to ensure that a patient is being effectively treated using electrical sub-threshold therapy.

In both conventional neuromodulation therapy described above where the patient feels paresthesia (super-threshold neuromodulation therapy) and sub-threshold neuromodulation therapy, common complications, caused due to cellular and synaptic mechanisms, include neurological phenomena, such as accommodation, adaption, and habituation, all of which entail a diminished neural response over time when there exists continuous input (in this case, electrical stimulation). For the purposes of this specification, we will use the term "accommodation" to generally refer to any mechanism that diminishes neural response due to continuous input.

Oftentimes, due to accommodation, a clinician may identify a modulation parameter set where a patient is obtaining great paresthesia, but when the clinician subsequently returns to this modulation parameter set, even within the same programming session, the patient may no longer receive the same paresthesia. While this complication may be tackled a little more easily in the case of super-threshold neuromodulation therapy, it is more difficult in the case of sub-threshold neuromodulation therapy because the clinician may not be able to determine, due to the lack of paresthesia, whether, and when, accommodation has occurred. Thus, without realizing that accommodation has occurred, the patient may continue receiving neuromodulation therapy but may receive little or no benefit from it.

There, thus, remains a need for an improved method and system that avoids or otherwise manages neurological accommodation caused by sub-threshold neuromodulation.

SUMMARY OF THE INVENTION

In accordance with a first aspect of the present inventions, a neuromodulation system comprises a plurality of electrical terminals configured for being respectively coupled to a plurality of electrodes, and modulation output circuitry configured for delivering electrical energy to the electrical terminals in accordance with at least one modulation parameter (e.g., an electrode combination (which may be fractionalized), a pulse amplitude, a pulse duration, a burst rate, a polarity, and/or a pulse rate). The neuromodulation system further comprises control circuitry configured for controlling the modulation output circuitry in an automated manner that varies the modulation parameters(s) over a period of time, such that the delivered electrical energy is continually maintained at a sub-threshold level throughout the period of time. The sub-threshold level may be referred to as a patient-perception threshold, which may be referred to as a boundary below which a patient does not sense delivery of the electrical energy. For example, in a spinal cord modulation system, The patient-perception threshold may be a boundary below which a patient does not experience paresthesia. In one embodiment, the modulation parameters may be varied in a manner such that neurological accommodation is avoided.

If the varied modulation parameter(s) comprises an electrode combination, the locus of the delivered electrical energy may be gradually displaced relative to the plurality of electrodes in one direction. The neuromodulation system may further comprise a casing containing the plurality of electrical terminals, the modulation output circuitry, and the control circuitry.

In one embodiment, the modulation output circuitry may be configured for varying the modulation parameter(s) by cycling through the sub-threshold modulation programs. In another embodiment, the delivered electrical energy comprises an electrical pulse train having a plurality of electrical pulse train portions respectively delivered to the electrical terminals in accordance with a plurality of modulation parameter sets that differ from each other by the at least one varied modulation parameter.

In an optional embodiment, the neuromodulation system further comprises memory configured for storing a predetermined tissue modulation regimen, in which case, the control circuitry is configured for controlling the modulation output circuitry to vary the modulation parameter(s) in accordance with the predetermined tissue modulation regimen. The predetermined tissue modulation regimen may be defined in a manner such that neurological accommodation is avoided.

In another optional embodiment, the neuromodulation system further comprises a user interface configured for receiving at least one patient satisfaction score, in which case, the control circuitry is configured for varying the modulation parameter(s) based on the patient satisfaction score(s). In still another optional embodiment, the neuromodulation system further comprises monitoring circuitry configured for detecting a physiological parameter, in which case, the control circuitry may be configured for varying the modulation parameter(s) based on the detected physiological parameter.

The neuromodulation system may optionally comprise memory configured for storing a limited range, wherein the control circuitry is configured for controlling the modulation output circuitry in the automated manner that varies one of the modulation parameter(s) within the limited range. For example, if the varied modulation parameter is a pulse rate, the limited range may have a lower pulse rate limit greater than 1500 Hz. If the varied modulation parameter is a pulse duration, the limited range may have an upper pulse duration limit lower than 500 µs. In some embodiments, the upper pulse duration limit may be lower than 100 µs.

In one optional embodiment, the control circuitry may be configured for varying the modulation parameter(s) until therapy provided by the delivered electrical energy is determined to be sufficient In another optional embodiment, the control circuitry may be configured for varying modulation parameter(s) to generate a plurality of different sets of modulation parameters, eliminating at least one of the different modulation parameter sets to create a reduced number of modulation parameter sets, and controlling the modulation output circuitry in an automated manner that serially delivers the electrical energy to the electrical terminals in accordance with the reduced number of modulation parameter sets.

The neuromodulation system may further comprise monitoring circuitry configured for detecting a physiological parameter in response to the delivery of the electrical energy to the electrical terminals as the modulation parameter(s) is varied, in which case, the control circuitry may be configured for eliminating the modulation parameter set(s) based on the detected physiological parameter. The neuromodulation system may alternatively further comprise a user interface configured for receiving input from a user (e.g., a patient satisfaction score) in response to the delivery of the electrical energy to the electrical terminals, in which case, the control circuitry may be configured for eliminating the modulation parameter set(s) based on the user input.

In still another optional embodiment, the control circuitry may be configured for varying the modulation parameter(s) to generate a plurality of different sets of modulation parameters, determining a therapeutic efficacy of a first one of the modulation parameter sets, and determining a second one of the modulation parameter sets based on the determined therapeutic efficacy of the first modulation parameter set. The second modulation parameter set may be determined by the control circuitry by, e.g., selecting the second modulation parameter sets from a plurality of pre-existing modulation parameter sets or by deriving a new modulation parameter set from the first modulation parameter set.

The neuromodulation system may further comprise monitoring circuitry configured for detecting a physiological parameter in response to the delivery of the electrical energy to the electrical terminals as the modulation parameter(s) is varied, in which case, the control circuitry may be configured for determining the therapeutic efficacy of the first modulation parameter set based on the detected physiological parameter. The neuromodulation system may alternatively further comprise a user interface configured for receiving input from a user (e.g., a patient satisfaction score) in response to the delivery of the electrical energy to the electrical terminals, in which case, the control circuitry may be configured for determining the therapeutic efficacy of the first modulation parameter set based on the user input.

In accordance with a second aspect of the present inventions, a method of providing therapy to a patient (e.g., the alleviation of chronic pain) is provided. The method comprises delivering electrical energy to tissue of the patient (e.g., spinal cord tissue) in accordance with at least one modulation parameter (e.g., an electrode combination (which may be fractionalized), a pulse amplitude, a pulse duration, a burst rate, a polarity, and/or a pulse rate), thereby providing therapy to the patient, and varying the at least one modulation parameter over a period of time, such that the delivered electrical energy is continually maintained at a sub-threshold level throughout the period of time. If the varied modulation parameter(s) comprises an electrode combination, the locus of the delivered electrical energy may be gradually displaced relative to the tissue. If the tissue comprises a spinal cord, and the locus of the delivered electrical energy may be gradually displaced rostro-caudally along the spinal cord or gradually displaced medio-laterally across the spinal cord.

In one method, the modulation parameter(s) is varied by cycling through a plurality of sub-threshold modulation programs. In another method, the delivered electrical energy comprises an electrical pulse train having a plurality of electrical pulse train portions respectively delivered to the tissue in accordance with a plurality of modulation parameter sets that differ from each other by the at least one varied modulation parameter.

One optional method further comprises storing a predetermined tissue modulation regimen, in which case, the modulation parameter(s) is varied in accordance with the predetermined tissue modulation regimen. The method may further comprise defining the predetermined tissue modulation regimen in a manner such that neurological accommodation is avoided.

Another optional method further comprises receiving at least one patient satisfaction score, in which case, the modulation parameter(s) is varied based on the patient satisfaction score(s). Still another optional method further comprises detecting a physiological parameter, in which case, the modulation parameter(s) is varied based on the detected physiological parameter.

The method may optionally comprise storing a limited range, in which case, one of the modulation parameter(s) is varied within the limited range. For example, if the varied modulation parameter is a pulse rate, the limited range may have a lower pulse rate limit greater than 1500 Hz. If the varied modulation parameter is a pulse duration, the limited range may have an upper pulse duration limit lower than 500 µs. In some embodiments, the upper pulse duration limit may be lower than 100 µs.

In one optional method, the modulation parameter(s) is varied until therapy provided by the delivered electrical energy is determined to be sufficient.

Another optional method further comprises varying the modulation parameter(s) to generate a plurality of different sets of modulation parameters, eliminating at least one of the plurality of different modulation parameter sets to create a reduced number of modulation parameter sets, and serially delivering the electrical energy to the patient in accordance with the reduced number of modulation parameter sets. The method may further comprise detecting a physiological parameter in response to the delivery of the electrical energy to the patient as the modulation parameter(s) is varied, in which case, the modulation parameter set(s) may be eliminated based on the detected physiological parameter. Or the method may further comprise receiving input from a user (e.g., a patient satisfaction score) in response to the delivery of the electrical energy to the patient, in which case, the modulation parameter set(s) may be eliminated based on the user input.

In still another optional method, the modulation parameter(s) is varied to generate a plurality of different sets of modulation parameters, and the method further comprising determining a therapeutic efficacy of a first one of the modulation parameter sets, and determining a second one of the modulation parameter sets based on the determined therapeutic efficacy of the first modulation parameter set. The second modulation parameter set may be determined by, e.g., selecting the second modulation parameter sets from a plurality of pre-existing modulation parameter sets or by deriving a new modulation parameter set from the first modulation parameter set.

The method may further comprise detecting a physiological parameter in response to the delivery of the electrical energy to the patient as the modulation parameter(s) is varied, in which case, the efficacy of the first modulation parameter set may be determined based on the detected physiological parameter. Or the method may further comprise receiving input from a user (e.g., a patient satisfaction score) in response to the delivery of the electrical energy to the patient, in which case, the efficacy of the first modulation parameter set may be determined based on the user input.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

The description that follows relates to a neuromodulation system in the form of a spinal cord modulation (SCM) system. However, it is to be understood that the while the invention lends itself well to applications in SCM, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

Figure 1:
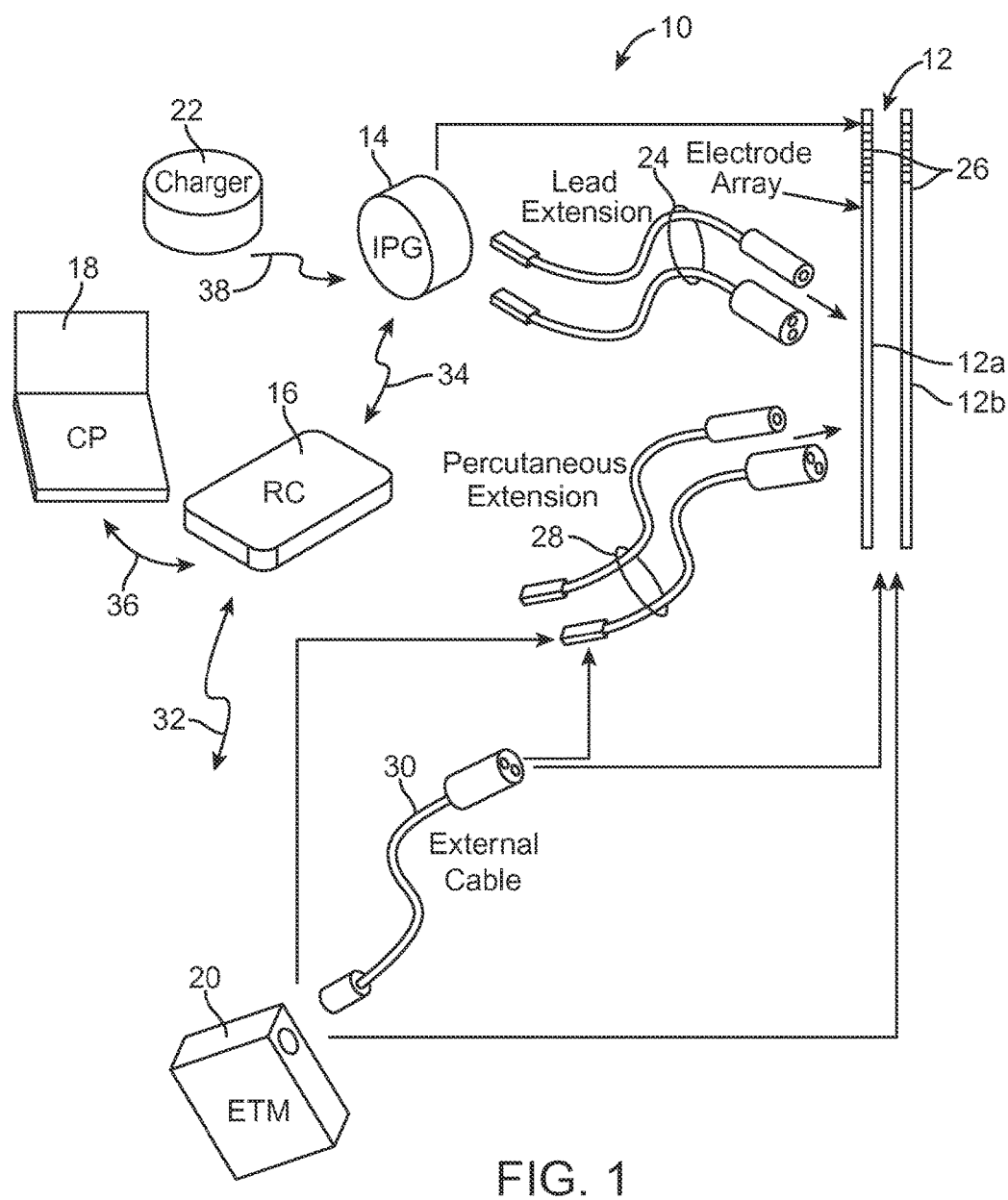
FIG. 1 is a plan view of a Spinal Cord Modulation (SCM) system constructed in accordance with one embodiment of the present inventions.

Turning first to FIG. 1, an exemplary SCM system 10, generally includes a plurality (in this case, two) of implantable neuromodulation leads 12, an implantable pulse generator (IPG) 14, an external remote controller RC 16, a clinician's programmer (CP) 18, an external trial modulator (ETM) 20, and an external charger 22.

The IPG 14 is physically connected via one or more percutaneous lead extensions 24 to the neuromodulation leads 12, which carry a plurality of electrodes 26 arranged in an array. In the illustrated embodiment, the neuromodulation leads 12 are percutaneous leads, and to this end, the electrodes 26 are arranged in-line along the neuromodulation leads 12. The number of neuromodulation leads 12 illustrated is two, although any suitable number of neuromodulation leads 12 can be provided, including only one. Alternatively, a surgical paddle lead in can be used in place of one or more of the percutaneous leads. As will be described in further detail below, the IPG 14 includes pulse generation circuitry that delivers electrical modulation energy in the form of a pulsed electrical waveform (i.e., a temporal series of electrical pulses) to the electrode array 26 in accordance with a set of modulation parameters.

The ETM 20 may also be physically connected via the percutaneous lead extensions 28 and external cable 30 to the neuromodulation leads 12. The ETM 20, which has similar pulse generation circuitry as the IPG 14, also delivers electrical modulation energy in the form of a pulse electrical waveform to the electrode array 26 accordance with a set of modulation parameters. The major difference between the ETM 20 and the IPG 14 is that the ETM 20 is a non-implantable device that is used on a trial basis after the neuromodulation leads 12 have been implanted and prior to implantation of the IPG 14, to test the responsiveness of the modulation energy delivered to the patient. Thus, any functions described herein with respect to the IPG 14 can likewise be performed with respect to the ETM 20.

The RC 16 may be used to telemetrically control the ETM 20 via a bi-directional RF communications link 32. Once the IPG 14 and neuromodulation leads 12 are implanted, the RC 16 may be used to telemetrically control the IPG 14 via a bi-directional RF communications link 34. Such control allows the IPG 14 to be turned on or off and to be programmed with different modulation parameter sets. The IPG 14 may also be operated to modify the programmed modulation parameters to actively control the characteristics of the electrical modulation energy output by the IPG 14. The CP 18 provides clinician detailed modulation parameters for programming the IPG 14 and ETM 20 in the operating room and in follow-up sessions.

The CP 18 may perform this function by indirectly communicating with the IPG 14 or ETM 20, through the RC 16, via an IR communications link 36. Alternatively, the CP 18 may directly communicate with the IPG 14 or ETM 20 via an RF communications link (not shown). The clinician detailed modulation parameters provided by the CP 18 are also used to program the RC 16, so that the modulation parameters can be subsequently modified by operation of the RC 16 in a stand-alone mode (i.e., without the assistance of the CP 18).

The external charger 22 is a portable device used to transcutaneously charge the IPG 14 via an inductive link 38. Once the IPG 14 has been programmed, and its power source has been charged by the external charger 22 or otherwise replenished, the IPG 14 may function as programmed without the RC 16 or CP 18 being present.

For purposes of brevity, the details of the CP 18, ETM 20, and external charger 22 will not be described herein. Details of exemplary embodiments of these devices are disclosed in U.S. Pat. No. 6,895,280, which is expressly incorporated herein by reference.

Figure 2:
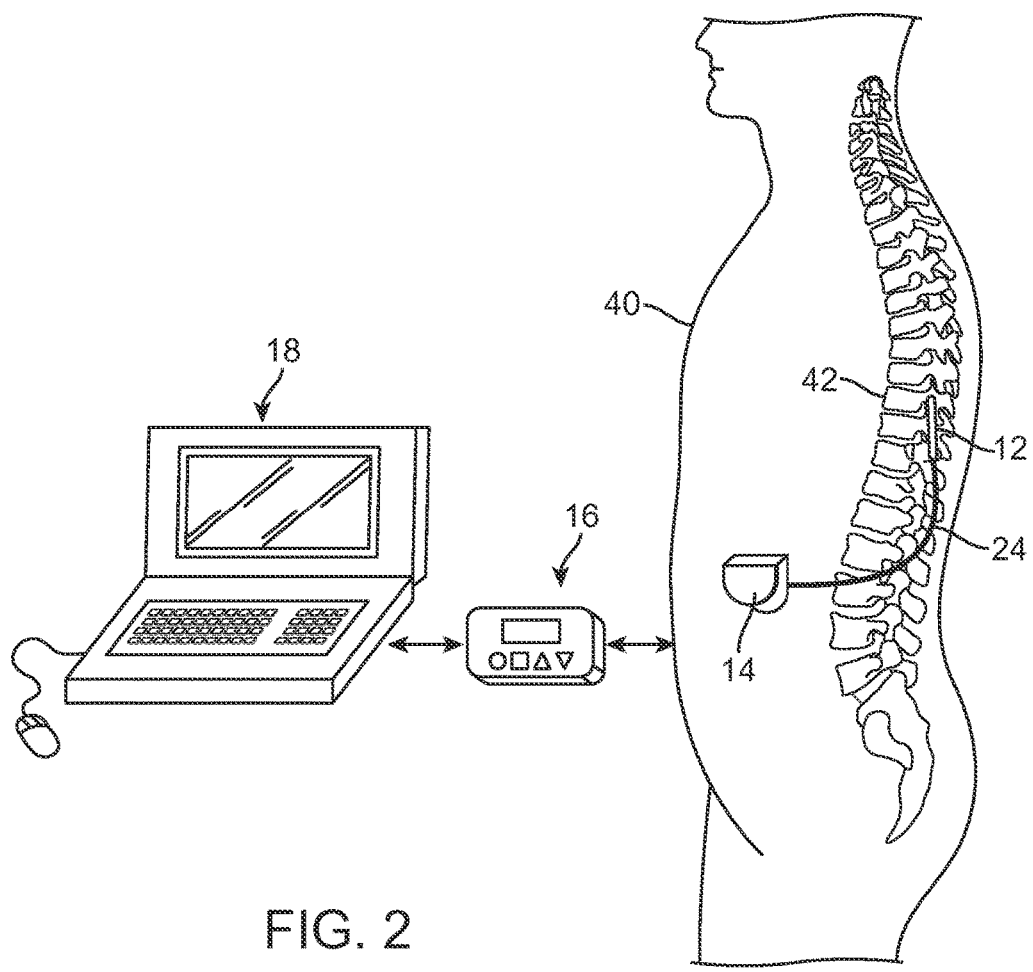
FIG. 2 is a plan view of the SCM system of FIG. 1 in use with a patient.

As shown in FIG. 2, the neuromodulation leads 12 are implanted within the spinal column 42 of a patient 40. The preferred placement of the neuromodulation leads 12 is adjacent, i.e., resting upon, the spinal cord area to be stimulated. Due to the lack of space near the location where the neuromodulation leads 12 exit the spinal column 42, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the neuromodulation leads 12. As there shown, the CP 18 communicates with the IPG 14 via the RC 16.

Figure 3:
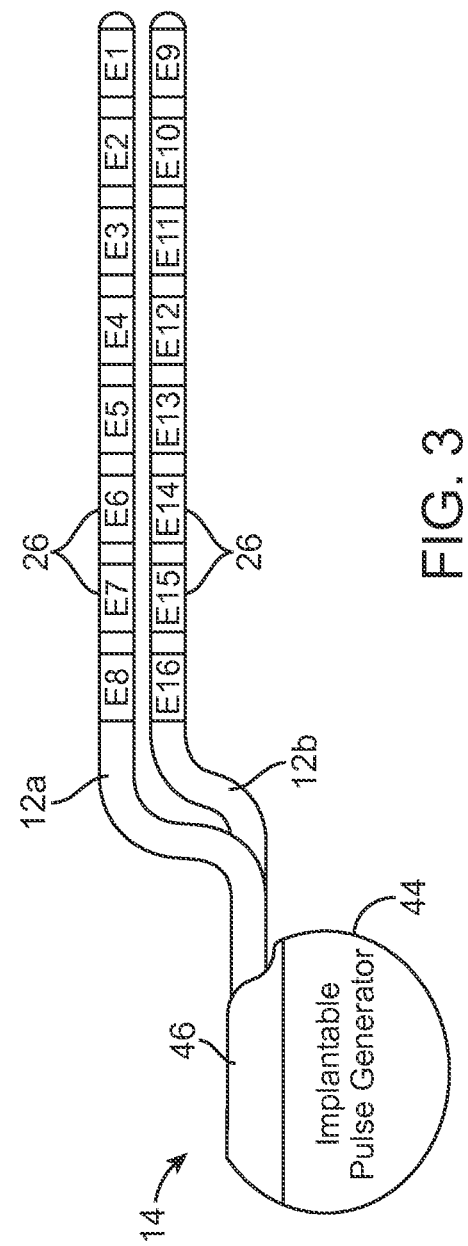
FIG. 3 is a profile view of an implantable pulse generator (IPG) and percutaneous leads used in the SCM system of FIG. 1.

Referring now to FIG. 3, the external features of the neuromodulation leads 12 and the IPG 14 will be briefly described. One of the neuromodulation leads 12a has eight electrodes 26 (labeled E1-E8), and the other neuromodulation lead 12b has eight electrodes 26 (labeled E9-E16). The actual number and shape of leads and electrodes will, of course, vary according to the intended application. The IPG 14 comprises an outer case 44 for housing the electronic and other components (described in further detail below), and a connector 46 to which the proximal ends of the neuromodulation leads 12 mates in a manner that electrically couples the electrodes 26 to the electronics within the outer case 44. The outer case 44 is composed of an electrically conductive, biocompatible material, such as titanium, and forms a hermetically sealed compartment wherein the internal electronics are protected from the body tissue and fluids. In some cases, the outer case 44 may serve as an electrode.

As will be described in further detail below, the IPG 14 includes a battery and pulse generation circuitry that delivers the electrical modulation energy in the form of one or more electrical pulse trains to the electrode array 26 in accordance with a set of modulation parameters programmed into the IPG 14. Such modulation parameters may comprise electrode combinations, which define the electrodes that are activated as anodes (positive), cathodes (negative), and turned off (zero), percentage of modulation energy assigned to each electrode (fractionalized electrode configurations), and electrical pulse parameters, which define the pulse amplitude (measured in milliamps or volts depending on whether the IPG 14 supplies constant current or constant voltage to the electrode array 26), pulse duration (measured in microseconds), pulse rate (measured in pulses per second), and burst rate (measured as the modulation on duration X and modulation off duration Y).

Figure 4:
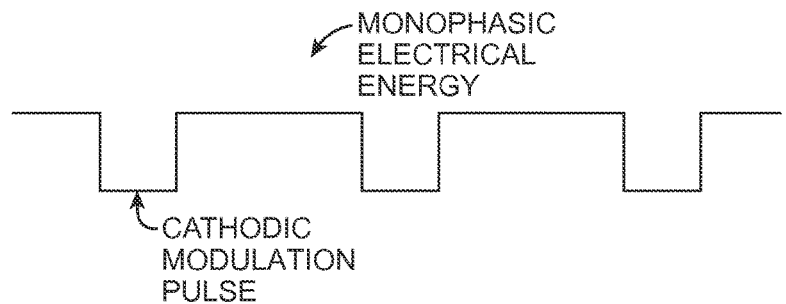
FIG. 4 is a plot of monophasic cathodic electrical modulation energy.

Electrical modulation will occur between two (or more) activated electrodes, one of which may be the IPG case 44. Modulation energy may be transmitted to the tissue in a monopolar or multipolar (e.g., bipolar, tripolar, etc.) fashion. Monopolar modulation occurs when a selected one of the lead electrodes 26 is activated along with the case of the IPG 14, so that modulation energy is transmitted between the selected electrode 26 and case. Bipolar modulation occurs when two of the lead electrodes 26 are activated as anode and cathode, so that modulation energy is transmitted between the selected electrodes 26. For example, electrode E3 on the first lead 12a may be activated as an anode at the same time that electrode E11 on the second lead 12a is activated as a cathode. Tripolar modulation occurs when three of the lead electrodes 26 are activated, two as anodes and the remaining one as a cathode, or two as cathodes and the remaining one as an anode. For example, electrodes E4 and E5 on the first lead 12a may be activated as anodes at the same time that electrode E12 on the second lead 12b is activated as a cathode The modulation energy may be delivered between a specified group of electrodes as monophasic electrical energy or multiphasic electrical energy. As illustrated in FIG. 4, monophasic electrical energy takes the form of an electrical pulse train that includes either all negative pulses (cathodic), or alternatively all positive pulses (anodic).

Figure 5A:
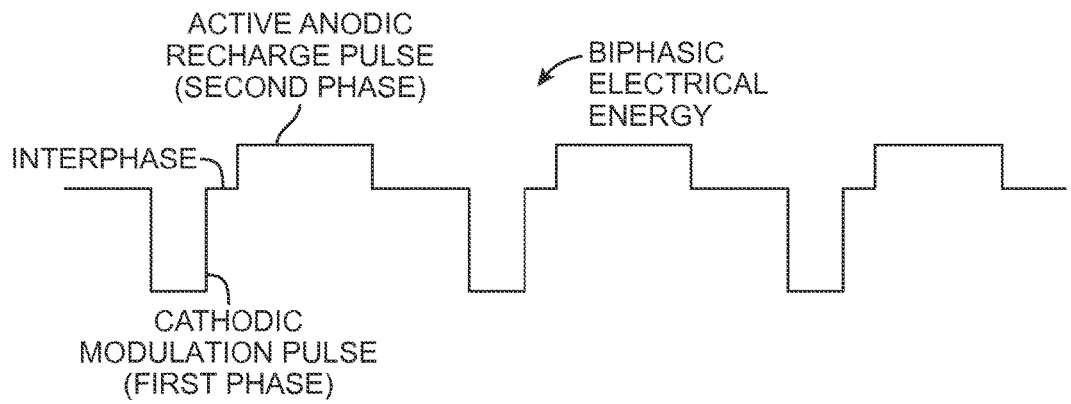
FIG. 5a is a plot of biphasic electrical modulation energy having a cathodic modulation pulse and an active charge recovery pulse.
Figure 5B:
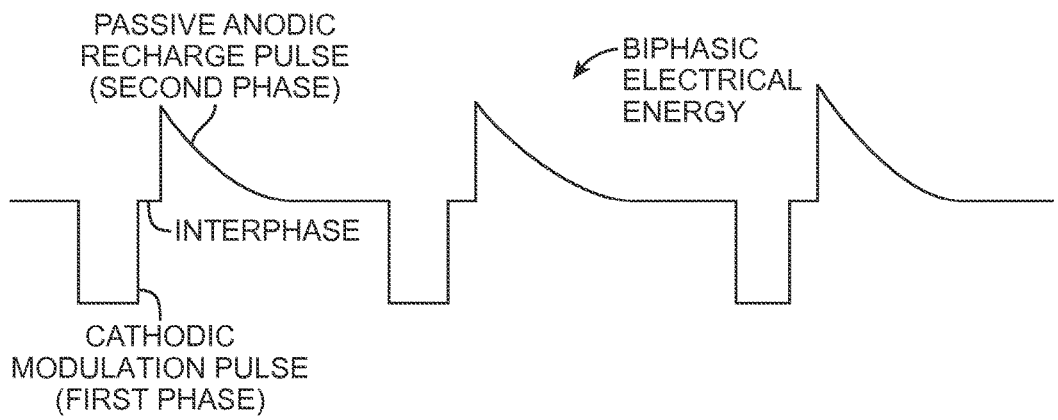
FIG. 5b is a plot of biphasic electrical modulation energy having a cathodic modulation pulse and a passive charge recovery pulse.

Multiphasic electrical energy includes a series of pulses that alternate between positive and negative. For example, as illustrated in FIGS. 5a and 5b, multiphasic electrical energy may include a series of biphasic pulses, with each biphasic pulse including a cathodic (negative) modulation pulse (during a first phase) and an anodic (positive) charge recovery pulse (during a second phase) that is generated after the modulation pulse to prevent direct current charge transfer through the tissue, thereby avoiding electrode degradation and cell trauma. That is, charge is conveyed through the electrode-tissue interface via current at an electrode during a modulation period (the length of the modulation pulse), and then pulled back off the electrode-tissue interface via an oppositely polarized current at the same electrode during a recharge period (the length of the charge recovery pulse).

The second phase may have an active charge recovery pulse (FIG. 5a), wherein electrical current is actively conveyed through the electrode via current or voltage sources, or the second phase may have a passive charge recovery pulse (FIG. 5b), wherein electrical current is passively conveyed through the electrode via redistribution of the charge flowing from coupling capacitances present in the circuit. Using active recharge, as opposed to passive recharge, allows faster recharge, while avoiding the charge imbalance that could otherwise occur. Another electrical pulse parameter in the form of an interphase can define the time period between the pulses of the biphasic pulse (measured in microseconds).

More significant to the present inventions, the SCM system 10 is configured for automatically varying modulation parameters of the delivered electrical energy over a period of time (i.e., the user does not manually select the modulation parameters), such that the delivered electrical energy, and in particular, an electrical pulse train, is continually maintained at a sub-threshold level during the time of treatment. To this end, the sub-threshold level treatment is operated on a limited range of modulation parameters (e.g., the sub-threshold electrical pulse train has a pulse rate greater than 1500 Hz, and a pulse duration less than 500 μs) that is expected to provide sub-threshold therapy. The SCM system 10 optionally is configured for receiving input from a user defining the limited range to best suit the needs of the patient.

In one embodiment, the SCM system 10 is configured for storing a predetermined tissue modulation regimen and varying the modulation parameters in accordance with the predetermined tissue modulation regimen. The predetermined tissue modulation regimen may be programmed into the IPG 14 depending on the particular needs of the patient. The predetermined tissue modulation regimen defines one or more sets of modulation parameters that are varied over time. The modulation parameters that may be varied may, e.g., include an electrode combination, a pulse amplitude, a pulse duration, a burst rate, a polarity, and/or a pulse rate. The predetermined tissue modulation regimen may be devised to ensure that the patient is receiving therapy from at least one portion of the electrical pulse train delivered as per the sub-threshold modulation program. For example, if any portion of the delivered electrical pulse train is deemed to provide efficacious therapy, it is believed that it will mitigate the chronic pain enough such that immediate therapy may not be needed during the periods when the delivered electrical pulse train may not provide therapy that may not be as efficacious or may not be efficacious at all.

The user may be able to program the predetermined tissue modulation regimen in accordance to the patient's preferences into the SCM system 10. Once the predetermined tissue modulation regimen is programmed, the SCM system 10 delivers the electrical pulse train and varies the selected one or more modulation parameters in accordance with which the electrical pulse train is delivered.

Figure 6A:
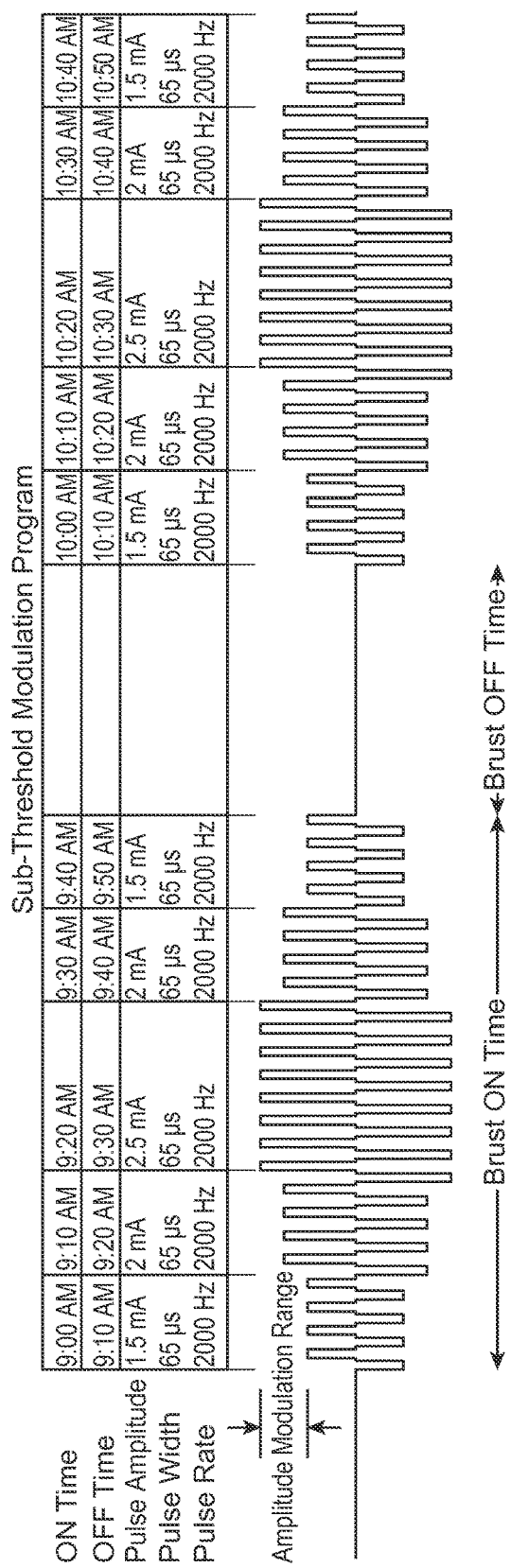
FIG. 6a is a timing diagram illustrating an electrical pulse train delivered by the SCM system of FIG. 1, wherein the pulse amplitude is varied as a function of time.

In one embodiment, the predetermined tissue modulation regimen defines a single sub-threshold modulation program that includes a modulation parameter that varies over time. For example, as shown in FIG. 6a, the SCM system 10 automatically varies the pulse amplitude of the electrical pulse train delivered to the patient. In the exemplary sub-threshold pulse train of FIG. 6a, the pulse amplitude of the electrical pulse train gradually varies over time (e.g., 1.5 mA to 2.5 mA), while the other modulation parameters remain constant. Thus, the amplitude modulation range of the electrical energy delivered to the patient changes seamlessly over time based on the modulation parameters set for the sub-threshold modulation program. The different pulse amplitudes can be cycled through multiple times (e.g., 1.5 mA to 2.5 mA the first time, 2.5 mA to 1.5 mA the second time, 1.5 mA to 2.5 mA the third time, 2.5 mA to 1.5 mA the fourth time, and so forth; or 1.5 mA to 2.5 mA the first time, 1.5 mA to 2.5 mA the second time, and so forth). Preferably, the lower limit of the amplitude modulation range is selected to be just above therapy threshold (i.e., the threshold at which therapy is achieved), and the upper limit of the amplitude modulation range is just below the threshold where paresthesia is perceived or otherwise an immediate physiological effect associated with the therapy is experienced.

Figure 6B:
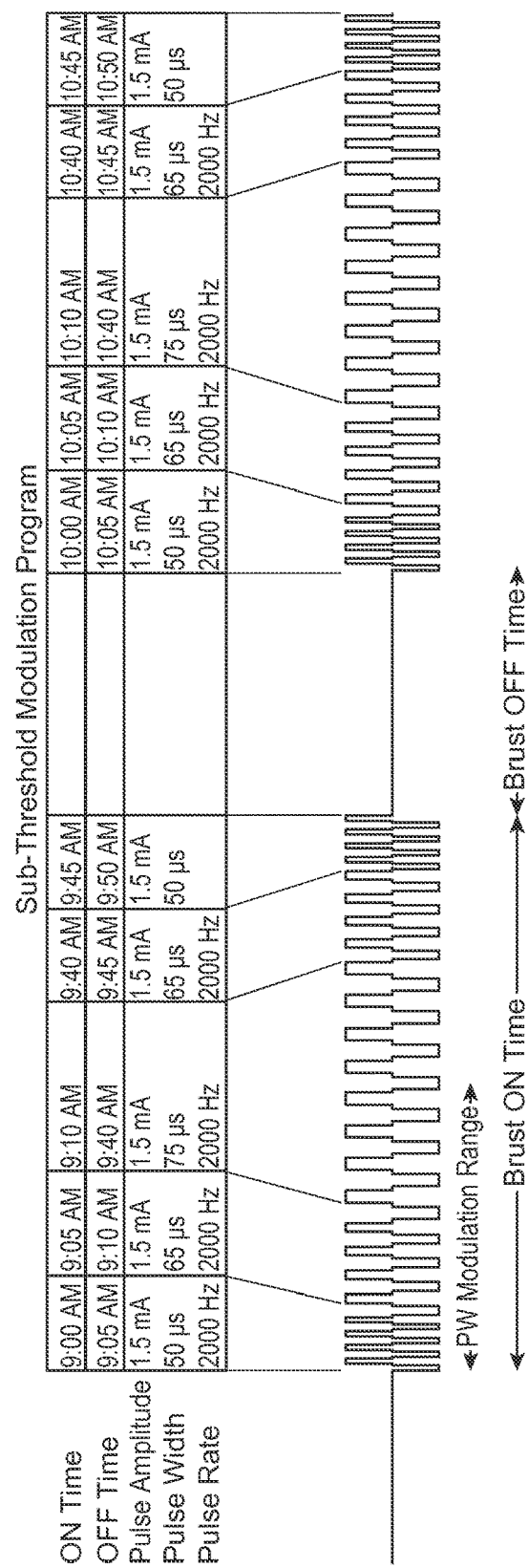
FIG. 6b is a timing diagram illustrating an electrical pulse train delivered by the SCM system of FIG. 1, wherein the pulse duration is varied as a function of time.

In another example shown in FIG. 6b, the SCM system 10 automatically varies the pulse duration of the electrical pulse train delivered to the patient. In the exemplary sub-threshold pulse train of FIG. 6b, the pulse duration of the electrical pulse train gradually varies over time (e.g., 50 μs to 75 μs), while the other modulation parameters remain constant. Thus, the pulse duration range of the electrical energy delivered to the patient changes seamlessly over time based on the modulation parameters set for the sub-threshold modulation program. The different pulse durations can be cycled through multiple times (e.g., 50 μs to 75 μs the first time, 75 μs to 50 μs the second time, 50 μs to 75 μs the third time, 75 μs to 50 μs the fourth time, and so on; or 50 μs to 75 μs the first time, 50 μs to 75 μs the second time, and so forth). Preferably, the lower limit of the pulse duration range is selected to be just above therapy threshold (i.e., the threshold at which therapy is achieved), and the upper limit of the pulse duration range is just below the threshold where paresthesia is perceived or otherwise an immediate physiological effect associated with the therapy is experienced.

As illustrated in FIGS. 6a and 6b, the electrical pulse train comprises a plurality of uniform electrical pulse train portions, each of which is delivered to the patient in accordance to its respective set of modulation parameters. Each uniform electrical pulse train portion differs from another uniform electrical pulse train portion by at least one varied modulation parameter (e.g., electrical pulse train portions that have varying pulse amplitude in FIG. 6a, or electrical pulse train portions that have varying pulse duration in FIG. 6b). In one or more embodiments, a time period of a uniform portion of the electrical pulse train may last anywhere between, e.g., 100 μs to one week depending on the patient's needs. Each uniform portion of the electrical pulse train typically lasts long enough to potentially provide therapy to the patient, and in some cases, long enough for the patient or clinician to reasonably decide if the uniform electrical pulse train portion was effective.

Figure 6C:
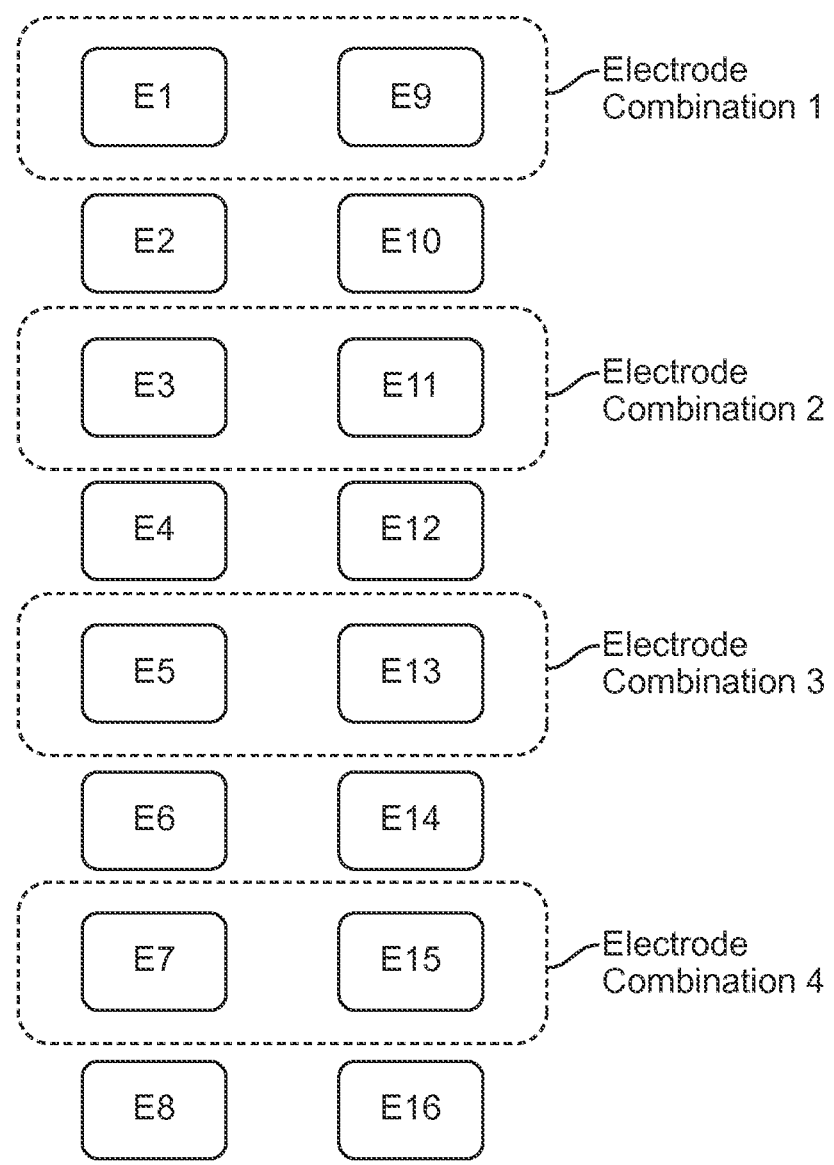
FIG. 6c is a schematic view of the electrode array illustrated in FIG. 3, wherein the electrode combination is varied by the SCM system of FIG. 1 as a function of time to generate four different electrode combinations.

In still another example shown in FIG. 6c, the SCM system 10 automatically varies the electrode combination used to deliver the electrical pulse train delivered to the patient. In particular, the electrode combination is varied, such that a locus of the electrical energy delivered to the patient is gradually displaced relative to the electrode array 26. For example, the electrical energy may first be delivered to electrodes E1, E9 (electrode combination 1), then electrodes E3, E11 (electrode combination 2), then electrodes E5, E13 (electrode combination 3), and then electrodes E7, E15 (electrode combination 4). Electrode combinations 1-4 can then be cycled through multiple times; for example, electrodes combinations 1, 2, 3, 4, 1, 2, 3, 4, 1, 2, 3, 4, etc. or electrode combinations 1, 2, 3, 4, 3, 2, 1, 2, 3, 4, 3, 2, 1, etc. In this manner, the locus of the electrical energy delivered to the spinal cord can be rostro-caudally displaced along the spinal cord. Alternatively, the electrical energy may be delivered to fractionalized electrode combinations that displace the locus of the electrical energy delivered to the spinal cord can be medio-laterally displaced across the spinal cord. For example, the electrical energy may be delivered to electrodes E4, E12 at the following fractionalization values in order: 100%, 0%; 75%, 25%; 50%, 50%; and 25%, 75%.

Although only one modulation parameter is varied in each of the examples illustrated above, it should be appreciated that the SCM system 10 is also capable of automatically varying more than one modulation parameter simultaneously. For example, both amplitude and pulse duration of a particular electrical pulse train may be varied over time. Although the sub-threshold electrical pulse trains are illustrated in FIGS. 6a and 6b as biphasic pulse trains having an active charge recovery phase, it should be appreciated that they can be biphasic cathodic or anodic pulse trains having a passive recovery phase.

Although the predetermined tissue modulation regimen has been described as defining only a single sub-threshold modulation program that varies a modulation parameter (that is different from each other by at least one modulation parameter), it should be appreciated that the predetermined tissue modulation regimen may define a plurality of sub-threshold modulation programs, in which case, the SCM system 10 may cycle through the sub-threshold modulation programs to vary the modulation parameters of the resulting electrical pulse train.

Figure 7:
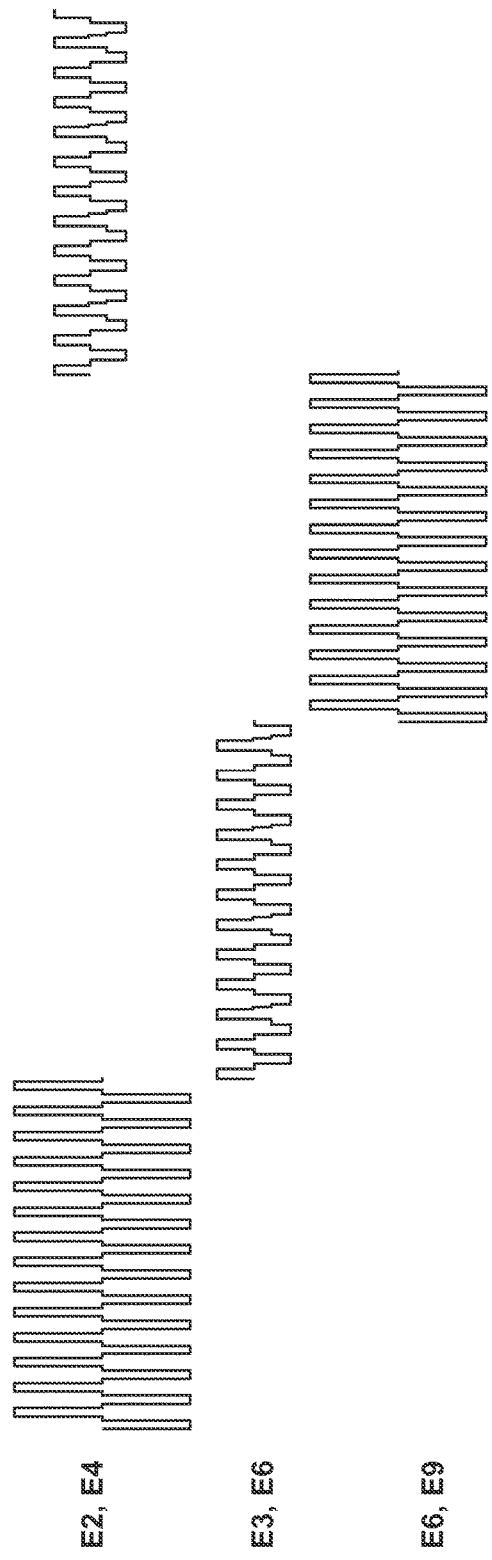
FIG. 7 is a timing diagram illustrating a plurality of sub-threshold modulation programs that are cycled through by the SCM system of FIG. 1.

For example, as illustrated in FIG. 7, the SCM system 10 cycles between Sub-Threshold Modulation Program 1, Sub-Threshold Modulation Program 2, Sub-Threshold Modulation Program 3, and Sub-Threshold Modulation Program 4. In cycling through the programs, the modulation parameters are automatically varied as defined in the four sub-threshold modulation programs.

In particular, the SCM system 10 first generates an electrical pulse train in accordance with a modulation parameter set defined by Sub-Threshold Modulation Program 1 (e.g., pulse amplitude of 2 mA, pulse duration of 65 µs, pulse rate of 2000 Hz, electrodes E2 and E4); then automatically generates an electrical pulse train in accordance with a different set of modulation parameters defined by Sub-Threshold Modulation Program 2 (e.g., pulse amplitude of 1 mA, pulse duration of 75 µs, pulse rate of 2000 Hz, electrodes E3 and E6); then automatically generates an electrical pulse train in accordance with a different set of modulation parameters defined by the Sub-Threshold Modulation Program 3 (e.g. pulse amplitude of 2 mA, pulse duration of 65 µs, pulse rate of 2000 Hz, electrodes E6 and E9), and then automatically generates an electrical pulse train in accordance with a different set of modulation parameters defined by Sub-Threshold Modulation Program 4 (e.g., pulse amplitude of 1 mA, pulse duration of 75 µs, pulse rate of 2000 Hz, electrodes E2 and E4).

Although each of the sub-threshold modulation programs have been illustrated as having a single set of modulation parameters for the duration of the respective sub-threshold modulation program, it can be appreciated that each sub-threshold modulation program may have different sets of modulation parameters (e.g., in a manner similar to that illustrated in FIG. 6a or FIG. 6b) for the duration of the sub-threshold modulation program.

As can be appreciated from the foregoing, the sub-threshold electrical pulse trains of sub-threshold modulation programs may be delivered to the same spinal cord tissue region or different spinal cord tissue regions depending on the modulation parameters of the sub-threshold modulation program. In the example illustrated in FIG. 7, Sub-Threshold Modulation Programs 1 and 4 are designed to deliver the electrical pulse trains to the same tissue region (i.e., both use the same electrode combination (i.e., via electrode combination E2 and E4), while Sub-Threshold Modulation Programs 2 and 3 are designed to deliver the electrical pulse trains to different tissue regions (i.e., via electrode combination E3, E6 and electrode combination E6, E9). Although the present inventions should not be so limited in their broadest aspects, the sub-threshold modulation programs do not overlap each other, such that when one sub-threshold modulation program terminates, the next program is automatically initiated.

Although each of the sub-threshold modulation programs has been described as having a single timing channel in the examples above, it should be appreciated that a sub-threshold modulation program may define a plurality of timing channels, in which case, the SCM system 10 simultaneously delivers electrical pulse trains to the patient as per the modulation parameters defined in the plurality of timing channels.

When the selected modulation parameter of the electrical pulse train is varied, a plurality of different modulation parameter sets are generated (e.g., modulation parameter sets that respectively correspond to the uniform electrical pulse train portions in FIGS. 6a and 6b, or modulation parameter sets that respectively correspond to the modulation programs in FIG. 7). Advantageously, the therapy provided by any of these different modulation parameter sets may be analyzed to determine which of the modulation parameter sets are most efficacious for the patient. Thus, by varying the electrical pulse train in any of the manner described above, different modulation parameter sets can be experimented with, such that the user may be able to arrive at the optimal set of modulation parameters that is ideal for the patient. During this process, one or more of the modulation parameter sets deemed not be efficacious may be eliminated. In the case where a modulation parameter set corresponding to a uniform electrical pulse portion of a single sub-threshold modulation program is eliminated, the remaining uniform electrical pulse portions will be consolidated to maintain a constant electrical pulse train. In the case where a modulation parameter set corresponding to one of a plurality of sub-threshold modulation programs is eliminated, the remaining sub-threshold modulation programs may be rescheduled to provide therapy during the time period when the eliminated sub-threshold modulation program would have been activated.

In one embodiment, the SCM system 10 may eliminate a modulation parameter set in response to user input to create a reduced number of modulation parameter sets. For example, the user may want to eliminate a particular modulation parameter set (e.g., a modulation parameter set corresponding to the portion of the electrical pulse train having a pulse amplitude of 5.0 mA (FIG. 6a) or corresponding to the portion of the electrical pulse train of 75 µs (FIG. 6b), or corresponding to Program 2 (FIG. 7)). Based on the user input (e.g., patient satisfaction scores discussed in further detail below), the SCM system 10 may eliminate the unwanted set of modulation parameters within the sub-threshold modulation program, thereby eliminating the portion of the electrical pulse train (FIG. 6a or FIG. 6b), or a sub-threshold modulation program (FIG. 7), from the predetermined tissue modulation regimen.

In another embodiment, the SCM system 10 may detect a physiological parameter (e.g., patient activity level, patient posture, etc.), and eliminate at least one modulation parameter set based on the physiological parameter. In one technique, the physical activity level of the patient is estimated from the magnitude of time varying electrical parameter data measured from the electrodes 26 or data measured from other sensors (impedance, activity, accelerometer, etc.), as described in U.S. patent application Ser. No. 12/024,947, entitled "Neurostimulation System and Method for Measuring Patient Activity," which is expressly incorporated herein by reference. In another technique, the physical activity level of the patient is estimated from a frequency that an orientation sensitive component implanted within the patient detects a change in orientation, as described in U.S. patent application Ser. No. 13/446,191, entitled "Sensing Device for Indicating Posture of Patient Implanted with a Neurostimulation Device, which is expressly incorporated herein by reference.

After detecting the physiological parameter, the SCM system 10 may automatically eliminate a set of modulation parameters from the electrical pulse train. For example, it can be assumed that the level of physical activity of a patient is inversely proportional to the pain level experienced by the patient (i.e., if the patient is awake and physically active, this indicates that current modulation parameter set is efficacious, whereas if the patient is excessively asleep or otherwise in the prone position, this indicates that the current modulation parameter set is not efficacious). Thus, if the SCM system 10 consistently detects low patient activity level during a portion of the electrical pulse train or during a particular modulation program, indicating that the modulation parameter set associated with that portion of the electrical pulse train or modulation program may not be efficacious, the SCM system 10 may automatically eliminate this modulation parameter set.

In any event, the SCM system 10 may vary the modulation parameters of the electrical pulse train over time based on a time schedule. In the case of an electrical pulse train delivered in accordance to a single sub-threshold modulation program (e.g., FIG. 6a and FIG. 6b), the time schedule dictates the duration of every set of modulation parameters that corresponds to its respective portion of the electrical pulse train in the time schedule. For example, in FIG. 6a, the pulse amplitude varies from 1.5 mA to 2 mA at 9:10 am as defined in the time schedule. Similarly, in FIG. 6b, the pulse duration varies from 50 μs to 60 μs based on the time schedule. Additionally, the time schedule also dictates the duration of every sub-threshold modulation program (e.g., FIG. 7). As illustrated in FIG. 7, the SCM system 10 switches from Sub-Threshold Modulation Program 1 to Sub-Threshold Modulation Program 1 at 11:00 am as defined in the time schedule. The time schedule may define a burst ON and OFF time for the electrical pulse train. In one technique, the time schedule may define absolute times for a particular set of modulation parameters or a particular sub-threshold modulation program (e.g., initiate Sub-Threshold Modulation Program 1 at 9:00 am, terminate Sub-Threshold Modulation Program 1 at 11:00 am, initiate Sub-Threshold Modulation Program 2 at 11:00 am. In another technique, the time schedule may define relative times for the set of modulation parameters or the sub-threshold modulation program (e.g., terminate Sub-Threshold Modulation Program 1 and initiate Sub-Threshold Modulation Program 2 two hours after Sub-Threshold Modulation Program 1 has been initiated). In yet another embodiment, the SCM system 10 modifies the time schedule based on user input.

Although the SCM system 10 has been described as cycling through the modulation parameter sets in accordance with a predetermined tissue modulation regimen, the SCM system 10 may optionally vary the modulation parameters sets in a more dynamic manner that is not predetermined. In particular, the SCM system 10 determines the next modulation parameter set in accordance with electrical pulse train will be delivered based on the therapeutic efficacy of the previous modulation parameter set(s). The next modulation parameter set may be pre-existing, in which case, the SCM system 10 selects one of the pre-existing modulation parameter sets as the next modulation parameter set in accordance with which the electrical pulse train will be delivered. Or, the SCM system 10 may dynamically derive a new modulation parameter set from the previous modulation parameter set and use that as the next modulation parameter set in accordance with which the electrical pulse train will be delivered.

In one particular embodiment, the SCM system 10 may deliver an electrical pulse train to the patient in accordance with a first set of modulation parameters and determine the therapeutic efficacy of the first modulation parameter set. As one example, the SCM system 10 may wait a predetermined period of time (e.g., 8 hours) and prompt the user to enter a patient satisfaction score indicative of the therapeutic efficacy of the first modulation parameters. The patient satisfaction score may range, e.g., from 0% (completely ineffective) to 100% (completely effective).

The SCM system 10 may then determine a second modulation parameter set based on the patient satisfaction score of the first modulation parameter set. If the patient satisfaction score is relatively high (e.g., at least 75%), the SCM system 10 may slightly vary a modulation parameter of the first modulation parameter set to arrive at the second modulation parameter set. For example, if the modulation parameter to be modified is the electrode combination, and the first modulation parameter set defines electrodes E2, E10 as cathodes, the second modulation parameter set may be defined to include electrodes E3, E11 (which are relatively close to electrodes E2, E10) if the patient satisfaction score of the first modulation parameter set is relatively high, and electrodes E8, E16 (which are relatively far away from electrodes E2, E10) if the patient satisfaction score of the first modulation parameter set is relatively low.

The SCM system 10 may then deliver an electrical pulse train to the patient in accordance with the second modulation parameter set. This process can be repeated (i.e., the therapeutic efficacy of the second modulation parameter set can be determined, a third modulation parameter set can be determined based on the determined therapeutic efficacy of the second modulation parameter set, an electrical pulse train can be delivered to the patient in accordance with the third modulation parameter set, the therapeutic efficacy of the third modulation parameter set can be determined, and so forth) until a sufficient number of modulation parameter sets having relatively high patient satisfaction scores are accumulated. The SCM system 10 may then incorporate these modulation parameter sets into a predetermined tissue modulation regimen (either in a single modulation program or multiple modulation programs) in the same manner described above. Alternatively, the modulation parameter sets can be tested until the therapeutic efficacy of the current modulation parameter set is sufficient, and this modulation parameter set is used to provide therapy to the patient.

The SCM system 10 may also analyze trends in previous modulation parameter sets to determine the next modulation parameter set. In one embodiment, if a modulation parameter is varied in one direction to respectively create first and second modulation parameter sets, and the second modulation parameter has a patient satisfaction score that is less than the first modulation parameter set, the SCM system 10 may vary the modulation parameter in the opposite direction to create a third modulation parameter set. For example, if the second modulation parameter set defines a pulse amplitude that is higher than the pulse amplitude defined by the first modulation parameter set, the third modulation parameter set may define a pulse amplitude less than that defined by the first modulation parameter set. In contrast, if the second modulation parameter set defines a pulse amplitude that is lower than the pulse amplitude defined by the first modulation parameter set, the third modulation parameter set may define a pulse amplitude higher than that defined by the first modulation parameter set.

In contrast, if a modulation parameter is varied in one direction to respectively create first and second modulation parameter sets, and the second modulation parameter has a patient satisfaction score that is higher than the first modulation parameter set, the SCM system 10 may vary the modulation parameter in the same direction to create a third modulation parameter set. For example, if the second modulation parameter set defines a pulse amplitude that is higher than the pulse amplitude defined by the first modulation parameter set, the third modulation parameter set may define a pulse amplitude even higher than that defined by the second modulation parameter set. In contrast, if the second modulation parameter set defines a pulse amplitude that is lower than the pulse amplitude defined by the first modulation parameter set, the third modulation parameter set may define a pulse amplitude that is even higher than that defined by the second modulation parameter set.

This trending concept can be applied to different electrode combinations. For example, if the modulation parameter that is varied is an electrode combination, the direction in which the locus of the delivered electrical energy is displaced can reversed by the third modulation parameter set if the patient satisfaction for the second modulation parameter set is less than the patient satisfaction for the first modulation parameter set (e.g., the first modulation parameter set may define electrodes E2, E9 as the cathodes, the second modulation parameter set may define electrodes E3, E10 as the cathodes, and the third modulation parameter set may define electrodes E1, E8 as the cathodes), and the direction in which the locus of the delivered electrical energy is displaced can be maintained by the third modulation parameter set if the patient satisfaction for the second modulation parameter set is greater than the patient satisfaction score for the first modulation parameter set (e.g., the first modulation parameter set may define electrodes E2, E9 as the cathodes, the second modulation parameter set may define electrodes E3, E10 as the cathodes, and the third modulation parameter set may define electrodes E4, E11 as the cathodes). Of course, the direction in which the locus of the delivered electrical energy is displaced may be defined using fractionalized electrode combinations.

Notably, although the SCM system 10 is described as determining the therapeutic efficacy of each of the modulation parameter sets based on patient satisfaction scores consciously entered by a user, the SCM system 10 may determine the therapeutic efficacy of each of the modulation parameter sets based on the detection of a physiological parameter (e.g., patient activity level, patient posture, etc.).

The physiological parameters may be detected in the manner described in U.S. patent application Ser. Nos. 12/024,947 and 13/446,191, which have been previously incorporated herein by reference.

Although the previous sections have discussed the automatic variance of modulation parameters in the context of finding the optimal set of modulation parameters for sub-threshold neuromodulation therapy, it should be appreciated that the same technique is also beneficial in avoiding (or limiting) neurological accommodation. Varying the modulation parameters on a consistent basis (e.g., per a time schedule as discussed previously) ensures that the neural tissue receiving the neuromodulation therapy continues to respond favorably but does not acclimate to any particular set of modulation parameters, thereby avoiding a state of neurological accommodation. As mentioned above, this is especially crucial in the case of sub-threshold neuromodulation therapy because the patient and/or clinician may be unaware that neurological accommodation has occurred and continue to receive sub-par treatment.

Keeping this in mind, the predetermined tissue modulation regimen may be devised specifically with the intent of avoiding neurological accommodation. Specifically, the predetermined tissue modulation may incorporate one or several techniques that will be described further below such that the patient receives a prescribed sub-threshold neuromodulation therapy, but the modulation parameters are timely varied such that nerve fibers of the targeted tissue do not accommodate to the prescribed sub-threshold therapy. When used to prevent neurological accommodation, the predetermined tissue modulation regimen, may either take the form of a single sub-threshold modulation program having multiple modulation parameter sets that are varied over time (e.g., FIG. 6a and FIG. 6b), or multiple sub-threshold modulation programs (e.g., FIG. 7) that are cycled through. For illustrative purposes, the following discussion will assume an exemplary predetermined tissue modulation regimen having a single sub-threshold modulation program that automatically varies the modulation parameters in at least one of the ways discussed below.

It should be appreciated that the automatic variance of modulation parameters, as shown in FIG. 6a (pulse amplitude) and FIG. 6b (pulse width) will have the effect of helping prevent neurological accommodation because the more variance that the modulation parameters exhibit, the less the chance that nerve fibers of the targeted tissue will neurologically accommodate to the therapy. Similarly, although not illustrated, varying the pulse rate in a similar fashion will also be effective in avoiding neurological accommodation. In a preferred embodiment these modulation parameters (i.e., pulse amplitude, pulse width, pulse rate) may be varied within a predetermined range (e.g., a range of pulse amplitude between 1.5 mA to 2.5 mA in FIG. 6a or a range of pulse width between 50 µs to 75 µs in FIG. 6b) such that the efficacy of the neuromodulation therapy is maintained without interrupting therapy. While varying the aforementioned modulation parameters is considered a good technique for preventing neurological accommodation, it should be noted that it results in the same nerve fibers getting stimulated (albeit to varying degrees) over a long period of time, thereby limiting its effectiveness.

One way of ensuring that nerve fibers are not being constantly stimulated is to vary the burst rate of electrical stimulation, providing the nerve fibers a respite from continuous stimulation. For example, referring to FIGS. 6a and 6b, the nerve fibers are stimulated from 9:00 AM at the start of the sub-threshold modulation program until "Burst OFF Time" at 9:50 AM, and again stimulated at 10:00 AM until 10:50 AM, giving a 10 minute break from electrical stimulation. In another example (not illustrated), the SCM system 10 may automatically burst stimulation on for 10 minutes, burst off stimulation for the next 10 minutes, and repeat the cycle for the duration of the sub-threshold modulation program. The burst rate may range from several times a second to several times an hour. This technique added to the automatic variance of pulse amplitude (FIG. 6a) or pulse width (FIG. 6b) may be more effective in preventing neurological accommodation.

Another technique for avoiding continuous electrical stimulation of the same nerve fibers is to vary the combination of electrodes that deliver electrical energy such that a different set of nerve fibers is stimulated. To this end, the SCM system 10 is configured for varying the electrode combinations (or fractionalized electrode combinations) in a manner that significantly modifies the locus of the electrical stimulation.

Assuming all the other modulation parameters are unchanged, moving the locus of electrical stimulation allows the patient to continue receiving efficacious neuromodulation therapy without constantly modulating the same nerve fibers. For example, referring back to FIG. 3, the SCM system 10 may automatically switch a cathodic current, and therefore the locus, from electrode E1 to electrode E8, then from electrode E8 to electrode E2, then from electrode E2 to electrode E7, then from electrode E7 to electrode E3, then from electrode E3 to electrode E6, then from electrode E6 to electrode E4, and then from electrode E4 to electrode E5. In another example, if two leads used, the SCM system 10 may automatically switch the cathodic current back and forth between the two leads (e.g., from electrode E1 to electrode E16, then from electrode E16 to electrode E2, from electrode E2 to electrode E15 and so forth) to provide even more variance of the locus.

It should be appreciated that the technique described above is different than the normal variance of electrode combinations, which more gradually varies the locus of stimulation (e.g., from electrode E1 to electrode E2, then from electrode E2 to electrode E3, then from electrode E4 to electrode E5 and so forth), and is therefore more apt to promote neurological accommodation.

In yet another technique that helps prevent neurological accommodation, the SCM system 10 is configured for automatically varying the polarity of the electrodes of a particular electrode combination. Specifically, the SCM system 10 automatically switches the polarity of the electrodes back and forth over a period of time such that electrodes that were designated as cathodes are automatically switched to being anodes, and the electrodes that were designated as anodes are automatically switched to being cathodes. In this case, even though the same electrode combination is used (i.e., the same nerve fibers are being stimulated), It has been observed that reversing the polarization of the electrical stimulation hyperpolarizes the spinal cord tissue, and therefore may help avoid, or limit, neurological accommodation.

For example, assuming that electrode E1 is initially configured as the cathode and the electrode E2 is configured as an anode, the SCM system 10 may automatically (e.g., based on a predetermined elapsed time, based on a predetermined number of pulses) switch the polarity of the electrodes such that electrode E1 is now configured as the anode and electrode E2 is configured as the cathode, thereby having the effect of hyperpolarizing the stimulated nerve fibers. After a predetermined period of time has elapsed or a predetermined number of pulses, the SCM system 10 may automatically switch back the polarity such that electrode E1 is once again configured as the cathode and electrode E2 is again configured as the anode, thereby stimulating the previously hyperpolarized tissue. It should be appreciated that in order to prevent any undesirable side effects, the remaining modulation parameters may be slightly altered when switching the polarity of the electrodes. For example, when in the first polarity, the electrode(s) may have a pulse amplitude that is less (e.g., one-third) than the pulse amplitude of the electrode(s) when in the second polarity. Similarly, other modulation parameters may be accordingly adjusted when reversing the polarity.

Thus, during the course of neuromodulation therapy, automatically varying the modulation parameters on a consistent basis in one or more of the aforementioned ways is beneficial for preventing neurological accommodation.

Figure 8:
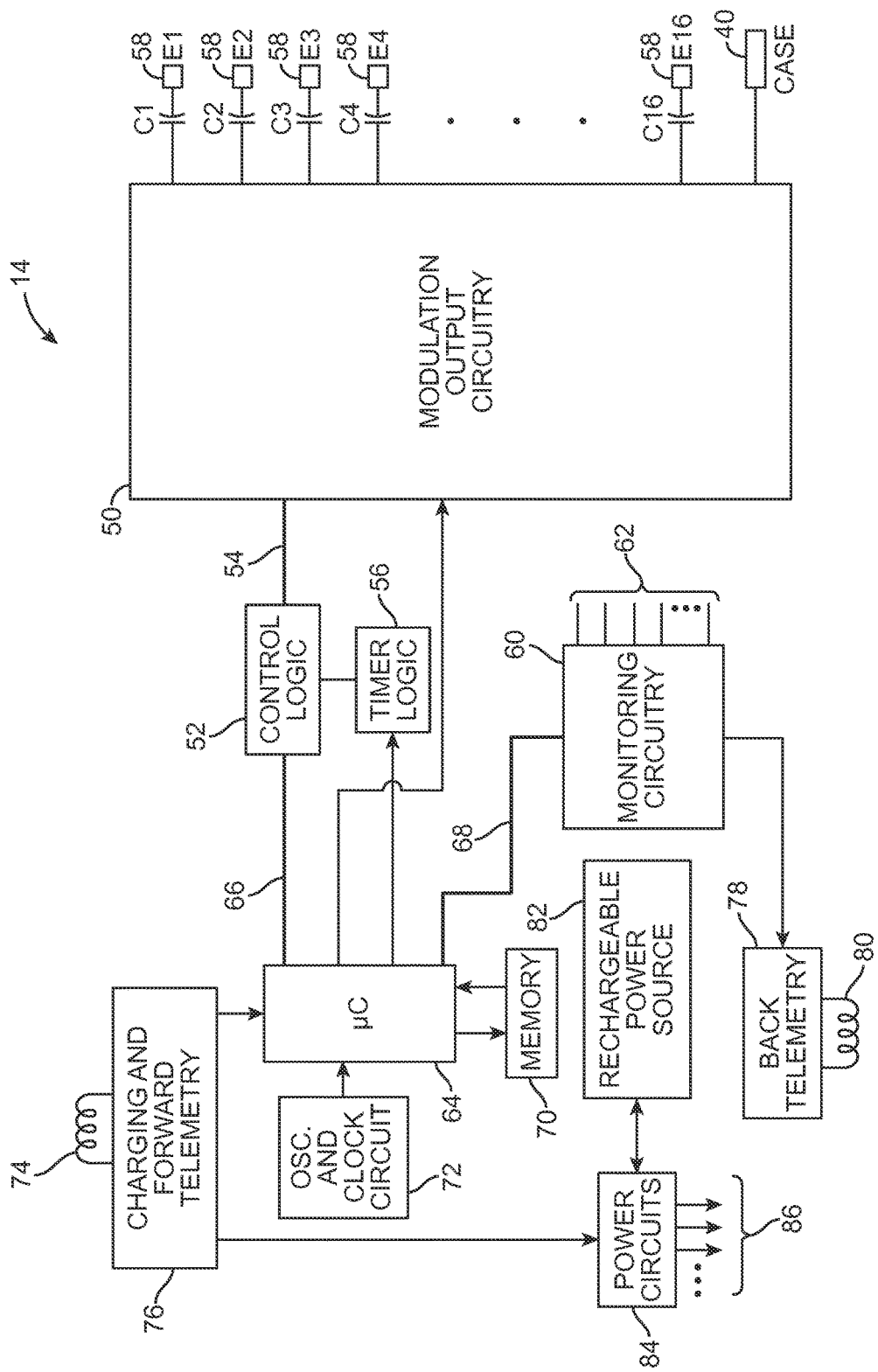
FIG. 8 is a block diagram of the internal components of the IPG of FIG. 3.

Turning next to FIG. 8, the main internal components of the IPG 14 will now be described. The IPG 14 includes modulation output circuitry 50 configured for generating electrical modulation energy in accordance with a defined pulsed waveform having a specified pulse amplitude, pulse rate, pulse duration, pulse shape, and burst rate under control of control logic 52 over data bus 54. Control of the pulse rate and pulse duration of the electrical waveform is facilitated by timer logic circuitry 56, which may have a suitable resolution, e.g., 10 μs. The modulation energy generated by the modulation output circuitry 50 is output via capacitors C1-C16 to electrical terminals 58 corresponding to the electrodes 26. The analog output circuitry 50 may either comprise independently controlled current sources for providing modulation pulses of a specified and known amperage to or from the electrodes 26, or independently controlled voltage sources for providing modulation pulses of a specified and known voltage at the electrodes 26.

Any of the N electrodes may be assigned to up to k possible groups or timing "channels." In one embodiment, k may equal four. The timing channel identifies which electrodes are selected to synchronously source or sink current to create an electric field in the tissue to be stimulated. Thus, multiple timing channels can be utilized to concurrently deliver electrical current (by interlacing the pulses of electrical pulse trains together) to multiple tissue regions of the patient. Amplitudes and polarities of electrodes on a channel may vary, e.g., as controlled by the RC 16. External programming software in the CP 18 is typically used to set modulation parameters including amplitude, pulse rate and pulse duration for the electrodes of a given channel, among other possible programmable features.

The N programmable electrodes can be programmed to have a positive (sourcing current), negative (sinking current), or off (no current) polarity in any of the k channels. Moreover, each of the N electrodes can operate in a multipolar (e.g., bipolar) mode, e.g., where two or more electrode contacts are grouped to source/sink current at the same time. Alternatively, each of the N electrodes can operate in a monopolar mode where, e.g., the electrodes associated with a channel are configured as cathodes (negative), and the case electrode (i.e., the IPG case) is configured as an anode (positive).

Further, the amplitude of the current pulse being sourced or sunk to or from a given electrode may be programmed to one of several discrete current levels, e.g., between 0 to 10 mA in steps of 0.1 mA. Also, the pulse duration of the current pulses is preferably adjustable in convenient increments, e.g., from 0 to 1 milliseconds (ms) in increments of 10 microseconds (μs). Similarly, the pulse rate is preferably adjustable within acceptable limits, e.g., from 0 to 50K pulses per second (pps). Other programmable features can include slow start/end ramping, burst modulation cycling (on for X time, off for Y time), interphase, and open or closed loop sensing modes.

The operation of this modulation output circuitry 50, including alternative embodiments of suitable output circuitry for performing the same function of generating modulation pulses of a prescribed amplitude and duration, is described more fully in U.S. Pat. Nos. 6,516,227 and 6,993,384, which are expressly incorporated herein by reference.

The IPG 14 further comprises monitoring circuitry 60 configured for monitoring the status of various nodes or other points 62 throughout the IPG 14, e.g., power supply voltages, temperature, battery voltage, and the like. The monitoring circuitry 60 may also be configured for measuring electrical parameter data from the electrodes 26 or other information from other sensors needed to determine the current activity level and/or posture of the patient.

The IPG 14 further comprises control circuitry in the form of a microcontroller (μC) 64 that controls the control logic over data bus 66, and obtains status data from the monitoring circuitry 60 via data bus 68. The IPG 14 additionally controls the timer logic 58. The IPG 14 further comprises memory 70 and oscillator and clock circuitry 72 coupled to the microcontroller 64. The microcontroller 64, in combination with the memory 70 and oscillator and clock circuitry 72, thus comprise a microprocessor system that carries out a program function in accordance with a suitable program stored in the memory 70. Alternatively, for some applications, the function provided by the microprocessor system may be carried out by a suitable state machine.

Thus, the microcontroller 64 generates the necessary control and status signals, which allow the microcontroller 64 to control the operation of the IPG 14 in accordance with a selected operating program and modulation program stored in the memory 70. In controlling the operation of the IPG 14, the microcontroller 64 is able to individually generate an electrical pulse train at the electrodes 26 using the modulation output circuitry 50, in combination with the control logic 52 and timer logic 56, thereby allowing each electrode 26 to be paired or grouped with other electrodes 26, including the monopolar case electrode. In accordance with modulation parameters stored within the memory 70, the microcontroller 64 may control the polarity, amplitude, rate, pulse duration and timing channel through which the modulation pulses are provided.

Thus, it can be appreciated that, under control of the microcontroller 64, the modulation output circuitry 50 is configured for outputting a k number of individual electrical pulse trains respectively in a k number of timing channels to the electrical terminals 56, with each electrical pulse train including bi-phasic pulses as shown in FIGS. 5a and 5b. The memory 70 may store a predetermined tissue modulation regimen comprising up to four sub-threshold modulation programs, with each sub-threshold modulation program having four timing channels. Thus, each sub-threshold modulation program defines four sets of modulation parameters for four respective timing channels. As discussed above, each sub-threshold modulation program may have sets of modulation parameters that vary over time such that each set of modulation parameters corresponds to a uniform portion of the electrical pulse train generated by the sub-threshold modulation program, or multiple sub-threshold modulation programs may be cycled through over time. Of course, the IPG 14 may have less or more than four sub-threshold modulation programs, and less or more than four timing channels for each modulation program. The memory 70 also stores a time schedule, which as discussed above, defines the beginning and end of a sub-threshold modulation program or a plurality of sub-threshold modulation programs. A modified time schedule may be stored in the memory based on user input. The memory 70 may optionally store any threshold values to which the electrical parameter measurements or other measurements are compared to facilitate determining whether patient activity is relatively high or relatively low.

The microcontroller 64 accesses one or more sub-threshold modulation programs from memory 70, and controls the modulation output circuitry 50 in a manner that automatically varies the modulation parameters of a single sub-threshold modulation program to generate a corresponding electrical pulse train and/or to cycle between the various sub-threshold modulation programs of a predetermined tissue modulation regimen. The microcontroller 64 can perform these functions based on the time schedule stored in the memory 70 or a determined patient activity level and/or posture. The microcontroller 64 may modify the time schedule based on user input to eliminate a portion of the electrical pulse train corresponding to a set of modulation parameters within a sub-threshold modulation program. Similarly, the microcontroller 64 may modify the time schedule based on user input to eliminate a sub-threshold modulation program entirely.

The IPG 14 further comprises an alternating current (AC) receiving coil 74 for receiving programming data (e.g., the operating program, modulation programs including the parameters, and/or a time schedule) from the RC 16 (shown in FIG. 1) in an appropriate modulated carrier signal, and charging and forward telemetry circuitry 76 for demodulating the carrier signal it receives through the AC receiving coil 74 to recover the programming data, which programming data is then stored within the memory 70, or within other memory elements (not shown) distributed throughout the IPG 14.

The IPG 14 further comprises back telemetry circuitry 78 and an alternating current (AC) transmission coil 80 for sending informational data sensed through the monitoring circuitry 60 to the RC 16. The back telemetry features of the IPG 14 also allow its status to be checked. For example, when the RC 16 initiates a programming session with the IPG 14, the capacity of the battery is telemetered, so that the external programmer can calculate the estimated time to recharge. Any changes made to the current stimulus parameters are confirmed through back telemetry, thereby assuring that such changes have been correctly received and implemented within the implant system. Moreover, upon interrogation by the RC 16, all programmable settings stored within the IPG 14 may be uploaded to the RC 16. Significantly, the back telemetry features allow raw or processed electrical parameter data (or other parameter data) previously stored in the memory 70 to be downloaded from the IPG 14 to the RC 16, which information can be used to track the physical activity of the patient.

The IPG 14 further comprises a rechargeable power source 82 and power circuitry 84 for providing the operating power to the IPG 14. The rechargeable power source 82 may, e.g., comprise a lithium-ion or lithium-ion polymer battery. The rechargeable battery 82 provides an unregulated voltage to the power circuitry 84. The power circuitry 84, in turn, generate the various voltages 86, some of which are regulated and some of which are not, as needed by the various circuits located within the IPG 14. The rechargeable power source 82 is recharged using rectified AC power (or DC power converted from AC power through other means, e.g., efficient AC-to-DC converter circuits, also known as "inverter circuits") received by the AC receiving coil 134. To recharge the power source 82, an external charger (not shown), which generates the AC magnetic field, is placed against, or otherwise adjacent, to the patient's skin over the implanted IPG 14. The AC magnetic field emitted by the external charger induces AC currents in the AC receiving coil 74. The charging and forward telemetry circuitry 76 rectifies the AC current to produce DC current, which is used to charge the power source 82. While the AC receiving coil 74 is described as being used for both wirelessly receiving communications (e.g., programming and control data) and charging energy from the external device, it should be appreciated that the AC receiving coil 74 can be arranged as a dedicated charging coil, while another coil, such as coil 80, can be used for bi-directional telemetry.

It should be noted that the diagram of FIG. 8 is functional only, and is not intended to be limiting. Those of skill in the art, given the descriptions presented herein, should be able to readily fashion numerous types of IPG circuits, or equivalent circuits, that carry out the functions indicated and described, which functions include not only producing a stimulus current or voltage on selected groups of electrodes, but also the ability to measure electrical parameter data at an activated or non-activated electrode.

Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference. It should be noted that rather than an IPG, the SCM system 10 may alternatively utilize an implantable receiver-modulator (not shown) connected to the modulation leads 12. In this case, the power source, e.g., a battery, for powering the implanted receiver, as well as control circuitry to command the receiver-modulator, will be contained in an external controller inductively coupled to the receiver-modulator via an electromagnetic link. Data/power signals are transcutaneously coupled from a cable-connected transmission coil placed over the implanted receiver-modulator. The implanted receiver-modulator receives the signal and generates the modulation in accordance with the control signals.

Figure 9:
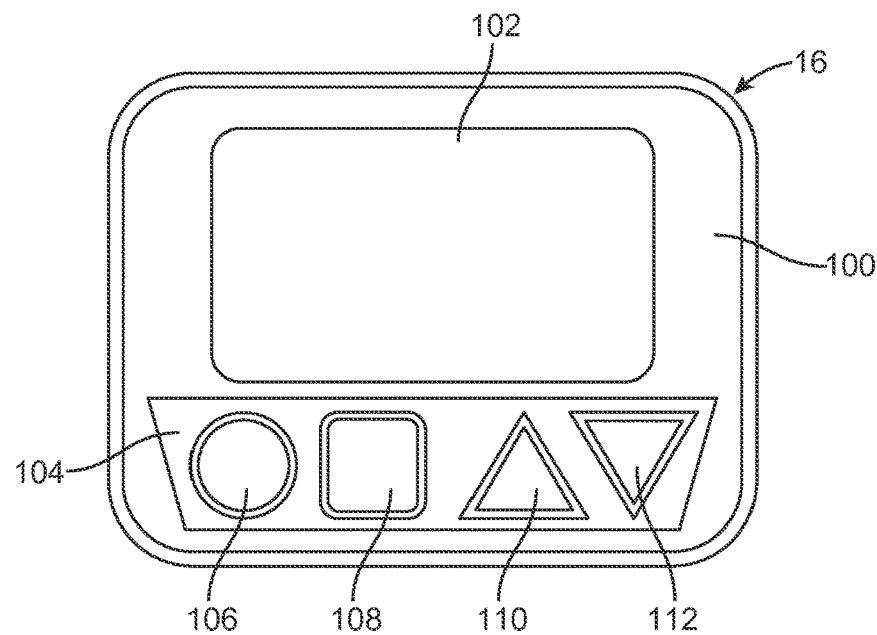
FIG. 9 is front view of a remote control (RC) used in the SCM system of FIG. 1.

Referring now to FIG. 9, one exemplary embodiment of an RC 16 will now be described. As previously discussed, the RC 16 is capable of communicating with the IPG 14, CP 18, or ETM 20. The RC 16 comprises a casing 100, which houses internal componentry (including a printed circuit board (PCB)), and a lighted display screen 102 and button pad 104 carried by the exterior of the casing 100. In the illustrated embodiment, the display screen 102 is a lighted flat panel display screen, and the button pad 104 comprises a membrane switch with metal domes positioned over a flex circuit, and a keypad connector connected directly to a printed circuit board (PCB). In an optional embodiment, the display screen 102 has touch-screen capabilities. The button pad 104 includes a multitude of buttons 106, 108, 110, and 112, which allow the IPG 14 to be turned ON and OFF, provide for the adjustment or setting of modulation parameters within the IPG 14, and provide for selection between screens.

In the illustrated embodiment, the button 106 serves as an ON/OFF button that can be actuated to turn the IPG 14 ON and OFF. The button 108 serves as a select button that can be actuated to switch the RC 16 between screen displays and/or parameters. The buttons 110 and 112 serve as up/down buttons that can be actuated to increment or decrement any of modulation parameters of the pulsed electrical train generated by the IPG 14, including pulse amplitude, pulse duration, and pulse rate. For example, the selection button 108 can be actuated to place the RC 16 in a "Pulse Amplitude Adjustment Mode," during which the pulse amplitude can be adjusted via the up/down buttons 110, 112, a "Pulse Width Adjustment Mode," during which the pulse width can be adjusted via the up/down buttons 110, 112, and a "Pulse Rate Adjustment Mode," during which the pulse rate can be adjusted via the up/down buttons 110, 112. Alternatively, dedicated up/down buttons can be provided for each modulation parameter. Rather than using up/down buttons, any other type of actuator, such as a dial, slider bar, or keypad, can be used to increment or decrement the modulation parameters. The selection button 108 can also be actuated to place the RC 16 in a "Scheduling Mode" to define or adjust a period of time for a portion of an electrical pulse train, and/or a beginning and ending of a sub-threshold modulation program. The selection button 108 may also be used to eliminate a portion of an electrical pulse train of a single sub-threshold modulation program, or to eliminate an entire sub-threshold modulation program. The RC 16 is also capable of receiving patient satisfaction scores from the user in response to the delivery of the electrical pulse train to the patient in accordance with the different modulation parameter sets.

Figure 10:
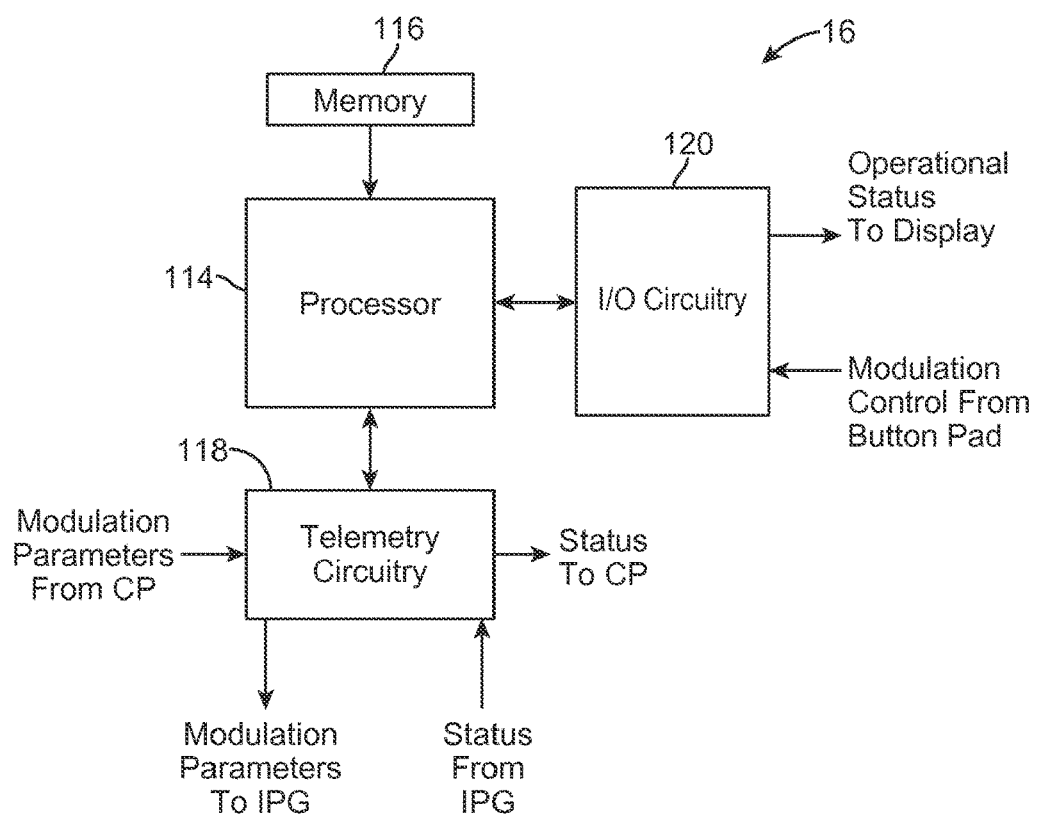
FIG. 10 is a block diagram of the internal components of the RC of FIG. 9.

Referring to FIG. 10, the internal components of an exemplary RC 16 will now be described. The RC 16 generally includes a controller/processor 64 (e.g., a microcontroller), memory 66 that stores an operating program for execution by the controller/processor 64, as well as modulation programs defining modulation parameter sets; input/output circuitry, and in particular, telemetry circuitry 68 for outputting modulation programs and scheduling information to the IPG 14 or otherwise directing the IPG 14 to deliver modulation energy in accordance with the modulation parameters and scheduling information, and receiving status information from the IPG 14; and input/output circuitry 70 for receiving modulation control signals from the button pad 104 or other control elements and transmitting status information to the display screen 102 (shown in FIG. 9).

Although, in the illustrated embodiment, the scheduling information is described as being transmitted from the RC 16 to the IPG 14, it should be appreciated that the RC 16 may simply transmit control signals to the IPG 14 to vary the modulation parameters corresponding to an electrical pulse train of a sub-threshold modulation program and/or to cycle through a plurality of sub-threshold modulation programs in accordance with the time schedule stored in the memory 66. The RC 16 may also transmit control signals to the IPG 14 to eliminate a portion of a sub-threshold modulation program or an entire sub-threshold modulation program and/or determine the current modulation parameter set based on the therapeutic efficacy of previous modulation parameter set(s), as discussed above. Further details of the functionality and internal componentry of the RC 16 are disclosed in U.S. Pat. No. 6,895,280, which has previously been incorporated herein by reference. Alternatively, these functions can be performed by the microcontroller 64 in the IPG 14.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A neuromodulation system for delivering a therapy to a patient, comprising:
modulation output circuitry and a plurality of electrical terminals, the plurality of electrical terminals configured to be respectively coupled to a plurality of electrodes, the modulation output circuitry being operably connected to the plurality of electrical terminals to deliver electrical energy to specified groups of electrodes for delivering the therapy to the patient, the modulation output circuitry configured to deliver electrical energy in accordance with sub-threshold programs, wherein each of the sub-threshold programs includes a set of modulation parameters for delivering the electrical energy below a patient-perception threshold, and the sub-threshold programs provide electrode fractionalization values that vary from one another; and
control circuitry configured to automatically control the modulation output circuitry to cycle through the sub-threshold programs that provide electrode fractionalization values that vary from one another over a period of time to continually maintain the delivered electrical energy below the patient-perception threshold over the period of time, the patient-perception threshold being a boundary below which the patient does not sense delivery of the electrical energy.

2. The neuromodulation system of claim 1, wherein:
the neuromodulation system includes a spinal cord modulation (SCM) system;
the patient-perception threshold being a boundary below which the patient does not experience paresthesia and above which the patient does experience paresthesia; and
the modulation system is configured to deliver therapeutic electrical energy effective to alleviate pain, including sub-threshold electrical energy effective to alleviate pain without paresthesia.

3. The neuromodulation system of claim 1, wherein the set of modulation parameters includes an electrode combination.

4. The neuromodulation system of claim 3, wherein the control circuitry is configured to automatically control the modulation output circuitry to cycle through the sub-threshold programs to gradually displace a locus of the delivered electrical energy relative to the plurality of electrodes.

5. The neuromodulation system of claim 1, wherein the set of modulation parameters includes a pulse amplitude, a pulse duration, and a pulse rate.

6. The neuromodulation system of claim 1, wherein the different sub threshold programs include different values for at least one of the pulse amplitude, the pulse duration or the pulse rate.

7. The neuromodulation system of claim 6, wherein at least one of the sub-threshold programs is configured to vary a value of at least one modulation parameter in the set of modulation parameters, and the modulation output circuitry is configured to vary the at least one modulation parameter.

8. The neuromodulation system of claim 7, further comprising memory configured to store a limited range, wherein the control circuitry is configured to automatically control the modulation output circuitry to vary the value of the at least one modulation parameter in the set of modulation parameters within the limited range.

9. The neuromodulation system of claim 8, wherein the at least one modulation parameter in the set of modulation parameters is a pulse rate or a pulse duration, and the limited range has a lower frequency limit greater than 1500 Hz, or the limited range has an upper pulse duration limit lower than 500 µs.

10. The neuromodulation system of claim 8, further comprising a user interface configured to receive input from a user defining the limited range.

11. The neuromodulation system of claim 7, wherein the delivered electrical energy comprises an electrical pulse train, wherein the electrical pulse train comprises a plurality of electrical pulse train portions respectively delivered to the electrical terminals in accordance with a plurality of modulation parameter sets that differ from each other by the varied modulation parameter.

12. The neuromodulation system of claim 7, wherein the control circuitry is configured to vary the modulation parameter to generate a plurality of different sets of modulation parameters, eliminate at least one of the plurality of different modulation parameter sets to create a reduced number of modulation parameter sets, and control the modulation output circuitry in an automated manner that serially delivers the electrical energy to the electrical terminals in accordance with the reduced number of modulation parameter sets, the system further comprising monitoring circuitry configured to detect a physiological parameter in response to the delivery of the electrical energy to the electrical terminals as the modulation parameter is varied, wherein the control circuitry is configured to eliminate the at least one modulation parameter set based on the detected physiological parameter.

13. The neuromodulation system of claim 7, wherein the control circuitry is configured to vary the modulation parameter to generate a plurality of different sets of modulation parameters, eliminate at least one of the plurality of different modulation parameter sets to create a reduced number of modulation parameter sets, and control the modulation output circuitry in an automated manner that serially delivers the electrical energy to the electrical terminals in accordance with the reduced number of modulation parameter sets, the system further comprising a user interface configured to receive input from a user in response to the delivery of the electrical energy to the electrical terminals, wherein the control circuitry is configured to eliminate the at least one modulation parameter set based on the user input.

14. The neuromodulation system of claim 7, wherein the control circuitry is configured to cycle through the sub-threshold programs to cycle through the different electrode fractionalization values to avoid neurological accommodation during delivery of a sub-threshold modulation therapy to alleviate pain without paresthesia.

15. The neuromodulation system of claim 7, further comprising a user interface configured to receive at least one patient satisfaction score, wherein the control circuitry is configured for varying the at least one modulation parameter based on the at least one patient satisfaction score.

16. The neuromodulation system of claim 7, wherein the control circuitry is configured to vary the at least one modulation parameter to generate a plurality of different sets of modulation parameters, determine a therapeutic efficacy of a first one of the modulation parameter sets, and determine a second one of the modulation parameter sets based on the determined therapeutic efficacy of the first modulation parameter set.

17. The neuromodulation system of claim 16, further comprising a user interface configured for receiving input from a user in response to the delivery of the electrical energy to the electrical terminals, wherein the control circuitry is configured for determining the therapeutic efficacy of the first modulation parameter set based on the user input, wherein the user input comprises a patient satisfaction score.

18. The neuromodulation system of claim 16, further comprising monitoring circuitry configured for configured for detecting a physiological parameter in response to the delivery of the electrical energy to the electrical terminals, wherein the control circuitry is configured for determining the therapeutic efficacy of the first modulation parameter set based on detected physiological parameter.

19. The neuromodulation system of claim 16, wherein the second modulation parameter set is determined by the control circuitry by selecting the second modulation parameter sets from a plurality of pre-existing modulation parameter sets.

20. The neuromodulation system of claim 16, wherein the second modulation parameter set is determined by the control circuitry by deriving a new modulation parameter set from the first modulation parameter set.

21. The neuromodulation system of claim 1, wherein the system includes a spinal cord modulation (SCM) system and the patient-perception threshold is a boundary below which a patient does not sense paresthesia.

22. An implantable neuromodulation device for delivering a therapy to a patient, comprising:
  implantable modulation output circuitry and a plurality of electrical terminals, the plurality of electrical terminals configured to be respectively coupled to a plurality of electrodes, the modulation output circuitry being operably connected to the plurality of electrical terminals to deliver electrical energy to specified groups of electrodes for delivering the therapy to the patient, the modulation output circuitry configured to deliver the electrical energy in accordance with sub-threshold programs, wherein each of the sub-threshold programs includes a set of modulation parameters for delivering the electrical energy below a patient-perception threshold, and the sub-threshold programs provide electrode fractionalization values that vary from one another; and
  implantable control circuitry configured to automatically control the implantable modulation output circuitry to cycle through the sub-threshold programs that provide electrode fractionalization values that vary from one another over a period of time to continually maintain the delivered electrical energy below a patient-perception threshold over the period of time, the patient-perception threshold being a boundary below which a patient does not sense delivery of the electrical energy.

23. The implantable neuromodulation device of claim 22, wherein the sub-threshold programs include different values for at least one of the pulse amplitude, the pulse duration or the pulse rate.

24. A non-transitory machine-readable medium including instructions, which when executed by a neuromodulation system having modulation output circuitry, a plurality of electrical terminals configured to be respectively coupled to a plurality of electrodes, and control circuitry, cause the neuromodulation system to:
  deliver electrical energy from the modulation output circuitry to specified groups of electrodes for delivering a therapy to a patient in accordance with sub-threshold programs, wherein each of the sub-threshold programs includes a set of modulation parameters for delivering the electrical energy below a patient-perception threshold, and the sub-threshold programs provide electrode fractionalization values that vary from one another; and
  control the modulation output circuitry, using the control circuitry, to automatically cycle through the sub-threshold programs that provide electrode fractionalization values that vary from one another over a period of time to continually maintain the delivered electrical energy below a patient-perception threshold over the period of time, the patient-perception threshold being a boundary below which a patient does not sense delivery of the electrical energy.

* * * * *